(12) United States Patent
Hung et al.

(10) Patent No.: US 8,673,625 B2
(45) Date of Patent: Mar. 18, 2014

(54) VALVED, MICROWELL CELL-CULTURE DEVICE AND METHOD

(75) Inventors: Paul Ju-Sung Hung, Fremont, CA (US); Philip Janmin Lee, Alameda, CA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/602,328

(22) Filed: Sep. 4, 2012

(65) Prior Publication Data
US 2013/0090268 A1    Apr. 11, 2013

Related U.S. Application Data

(62) Division of application No. 11/648,207, filed on Dec. 29, 2006, now Pat. No. 8,257,964.

(60) Provisional application No. 60/756,399, filed on Jan. 4, 2006.

(51) Int. Cl.
*C12M 1/34*    (2006.01)
*G01N 33/543*    (2006.01)

(52) U.S. Cl.
CPC .............................. *G01N 33/54366* (2013.01)
USPC ......... 435/287.1; 422/502; 264/226; 156/228

(58) Field of Classification Search
USPC ............ 435/287.1; 506/37; 264/81, 219, 227, 264/241; 156/228; 436/43, 180; 422/50, 81, 422/82, 502
See application file for complete search history.

(56) References Cited

U.S. PATENT DOCUMENTS

| 4,055,613 A | 10/1977 | Kapral |
| 4,661,455 A | 4/1987 | Hubbard |
| 4,734,373 A | 3/1988 | Bartal |
| 4,748,124 A | 5/1988 | Volger |

(Continued)

FOREIGN PATENT DOCUMENTS

| DE | 19948087 | 5/2001 |
| DE | 19948087 A1 | 5/2001 |

(Continued)

OTHER PUBLICATIONS

Chang et al. (2006) "Fabrication of polymer microlens arrays using capillary forming with a soft mold of microholes array and UV-curable polymer." Optical Society of America 14(13): 6253-6258.

(Continued)

*Primary Examiner* — Michael Hobbs
(74) *Attorney, Agent, or Firm* — Nields, Lemack & Frame, LLC

(57) ABSTRACT

A valved microfluidics device, microfluidics cell-culture device and system incorporating the devices are disclosed. The valved microfluidics device includes a substrate, a microchannel through which liquid can be moved from one station to another within the device, and a pneumatic microvalve adapted to be switched between open and closed states to control the flow of fluid through a microchannel. The microvalve is formed of three flexible membranes, one of which is responsive to pneumatic pressure applied to the valve and the other two of which deform to produce a more sealable channel cross-section. The cell culture device provides valving to allow controlled loading of cells into the individual well of the device, and exchange of cell-culture components in the wells.

12 Claims, 42 Drawing Sheets

(56) References Cited

U.S. PATENT DOCUMENTS

| | | | |
|---|---|---|---|
| 5,079,168 A | 1/1992 | Amiot |
| 5,153,131 A | 10/1992 | Wolf et al. |
| 5,310,676 A | 5/1994 | Johansson et al. |
| 5,330,908 A | 7/1994 | Spaulding |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wold et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Coble et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Change et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Griffith et al. |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 2002/0039785 A1 | 4/2002 | Schroeder et al. |
| 2002/0108860 A1 | 8/2002 | Staats |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Mehta et al. |
| 2004/0132175 A1 | 7/2004 | Vetillard et al. |
| 2004/0202579 A1 | 10/2004 | Larsson |
| 2004/0229349 A1 | 11/2004 | Daridon |
| 2004/0238484 A1 | 12/2004 | Le Pioufle |
| 2005/0009179 A1 | 1/2005 | Gemmiti et al. |
| 2005/0019213 A1 | 1/2005 | Kechagia et al. |
| 2005/0032208 A1 | 2/2005 | Oh et al. |
| 2005/0072946 A1* | 4/2005 | Studer et al. ............ 251/11 |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0128715 A1 | 6/2007 | Vukasinovic et al. |
| 2007/0264705 A1 | 11/2007 | Dodgson |
| 2007/0275455 A1 | 11/2007 | Hung et al. |
| 2008/0085556 A1 | 4/2008 | Graefing et al. |
| 2008/0176318 A1 | 7/2008 | Wilson et al. |
| 2008/0194012 A1 | 8/2008 | Lee et al. |
| 2008/0227176 A1 | 9/2008 | Wilson et al. |
| 2008/0233607 A1 | 9/2008 | Yu et al. |
| 2009/0023608 A1 | 1/2009 | Hung et al. |
| 2009/0123961 A1 | 5/2009 | Meyvantsson et al. |
| 2009/0203126 A1 | 8/2009 | Hung et al. |
| 2012/0003732 A1 | 1/2012 | Hung et al. |
| 2013/0059322 A1 | 3/2013 | Hung et al. |

(56) References Cited

U.S. PATENT DOCUMENTS

| | | |
|---|---|---|
| 2013/0081757 A1 | 4/2013 | Hung et al. |
| 2013/0171679 A1 | 7/2013 | Lee et al. |
| 2013/0171682 A1 | 7/2013 | Hung et al. |

FOREIGN PATENT DOCUMENTS

| | | |
|---|---|---|
| EP | 0155237 A2 | 9/1985 |
| EP | 0155237 | 9/1995 |
| EP | 0725134 | 8/1996 |
| EP | 0890636 | 1/1999 |
| GB | 1539263 | 1/1979 |
| WO | WO 91/15570 | 10/1991 |
| WO | WO 00/56870 | 9/2000 |
| WO | WO 00/60352 | 10/2000 |
| WO | WO 00/78932 | 10/2000 |
| WO | WO 01/92462 | 12/2001 |
| WO | WO 03/085080 | 10/2003 |
| WO | WO 2003/098218 | 11/2003 |
| WO | WO 2004/059299 | 7/2004 |
| WO | WO 2004/106484 | 12/2004 |
| WO | WO 2005/035728 | 4/2005 |
| WO | 2007/008609 A1 | 1/2007 |
| WO | WO 2007/008606 | 1/2007 |

OTHER PUBLICATIONS

Chao et al. (2007) "Rapid frabrication of microchannels using microscale plasma activated templating (μPLAT) generating water molds." The Rolay Society of Chemistry, 7: 641-643.

Degenaar et al. (2001) "A Method of Micrometer Resolution Patterning of Primary Culture Neurons for SPM Analysys." J. Bio Chem. 367-376.

Lee et al. (2007) "Microfluidic System for Automated Cell-Based Assays." JALA. 1-19.

Lim et al. (2003) "Fabrication of Microfludic Mixers and Artifical Vasculatures Using a High-Brightness Diode-Pumped Nd:YAG Lader Direct Write Method." Lap Chip 3: 318-323.

Runyon et al. (2004) Minimal Functional Model of Hemistasis in a Biomimetic Microfluidit System. Amgew Chem. Intl. Ed. 43: 1531-1536.

Tan et al. (2003) "Microfludic Patterning of Cellular Biopolymer Matrices for Biomimetic 3-D structures." Biomedical Microdivices 5(3): 235-244.

CellASIC Corporation (2012) "ONIX Application Note: microincubator for long term.".

Hung et al. (2005) "Continuous perfusion microfludic cell culture array for high—throughput cell-bases assays." Biotechnigues and Bioengineering 89(1): 1-8.

Lee et al. (2007) "Microfluidic System for Automated Cell-Based Assays." Lab Chip 9(1): 164-166.

Lee et al. (2007) "Microfluidic System for Automated Cell-Based Assays." JALA 12(6): 363-367.

Ong et al. (2008) "A gel-free 3D microfluidic cell culture system." Biomaterials 29(22): 3237-3244.

Extended European Search Report mailed Apr. 3, 2012 in European patent application No. EP 06786499.

International Search Report and Written Opinion mailed Apr. 9, 2009 in PCT application No. PCT/US06/26364 (corresponding to U.S. Appl. No. 11/994,997).

International Search Report and Written Opinion mailed Jul. 30, 2009 in PCT application No. PCT/US2009/030168.

Extended European Search report mailed Oct. 21, 2013 in European patent application No. EP 09701350.

International Search Report mailed May 14, 2013 in PCT application No. PCT/US2013/024999.

International Search Report mailed Mar. 19, 2013 in PCT application No. PCT/US2012/067632.

Lab Chip, 2005, vol. 5, No. 4, pp. 401-406, "Human neural stem growth and differentiation in a gradient-generating microfluidic device", Chung, et al.

Lab Chip, 2008, vol. 8, No. 1, pp. 34-57, "Biomolecular gradients in cell culture systems", Keenan, et al.

Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.

Lab Chip, 2009, vol. 9, No. 1, pp. 164-166, "Dynamic cell culture: a microfluidic function generator for live cell microscopy", Lee, et al.

Office Action mailed Feb. 22, 2013 in corresponding U.S. Appl. No. 13/602,331.

Office Action mailed Jun. 17, 2010 in co-pending U.S. Appl. No. 12/019,857.

Final Rejection mailed Feb. 28, 2011 in co-pending U.S. Appl. No. 12/019,857.

Office Action mailed Sep. 15, 2011 in co-pending U.S. Appl. No. 12/019,857.

Final Rejection mailed May 31, 2012 in co-pending U.S. Appl. No. 12/019,857.

Office Action—Restriction—mailed Jul. 13, 2011 in co-pending U.S. Appl. No. 12/348,907.

Office Action mailed Dec. 23, 2011 in co-pending U.S. Appl. No. 12/348,907.

Final Rejection mailed Sep. 17, 2012 in co-pending U.S. Appl. No. 12/348,907.

Office Action Nov. 28, 2012 in co-pending U.S. Appl. No. 13/011,857.

Final Rejection mailed Aug. 14, 2013 in co-pending U.S. Appl. No. 13/011,857.

Office Action—Restriction—mailed Feb. 22, 2013 in co-pending U.S. Appl. No. 13/436,992.

Office Action mailed Sep. 6, 2013 in co-pending U.S. Appl. No. 13/436,992.

Office Action—Restriction—mailed Oct. 16, 2013 in co-pending U.S. Appl. No. 13/692,869.

Office Action—Restriction—mailed Oct. 7, 2013 in co-pending U.S. Appl. No. 13/761,130.

Office Action—Restriction—mailed Mar. 9, 2011 in co-pending U.S. Appl. No. 11/994,997.

Office Action mailed Jul. 18, 2011 in co-pending U.S. Appl. No. 11/994,997.

Final Rejection mailed Feb. 8, 2012 in co-pending U.S. Appl. No. 11/994,997.

Office Action mailed Sep. 11, 2013 in co-pending U.S. Appl. No. 11/994,997.

Notice of Allowance mailed Nov. 13, 2013 in corresponding U.S. Appl. No. 13/602,331.

\* cited by examiner

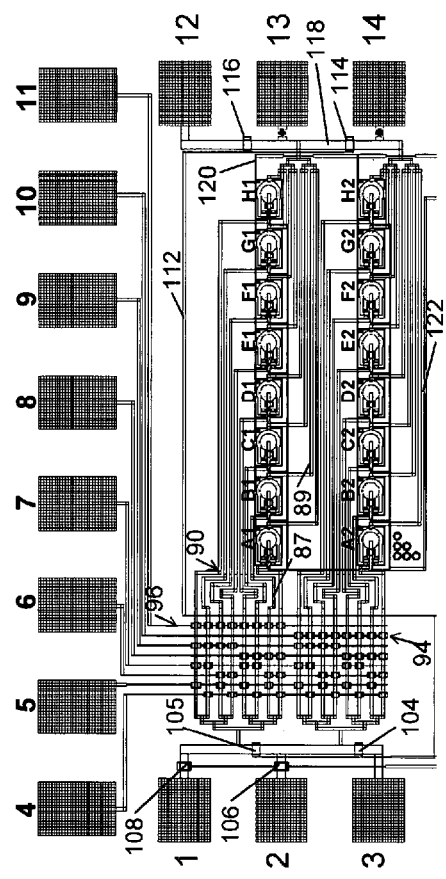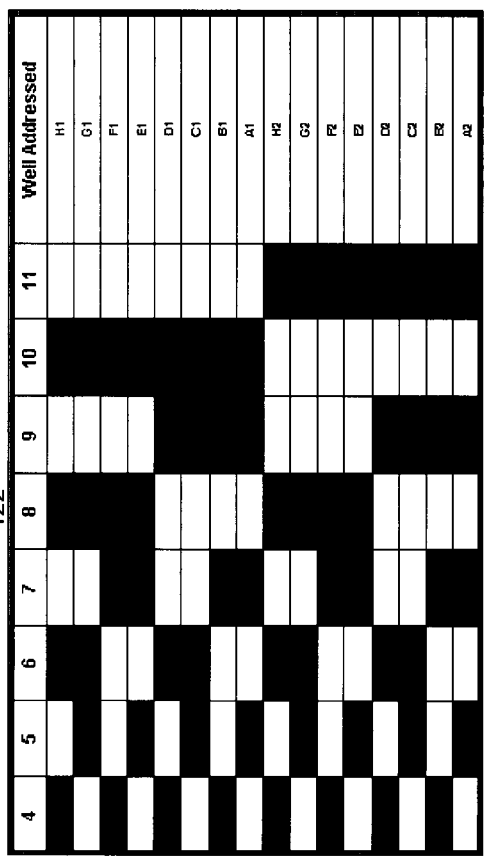
Fig. 4

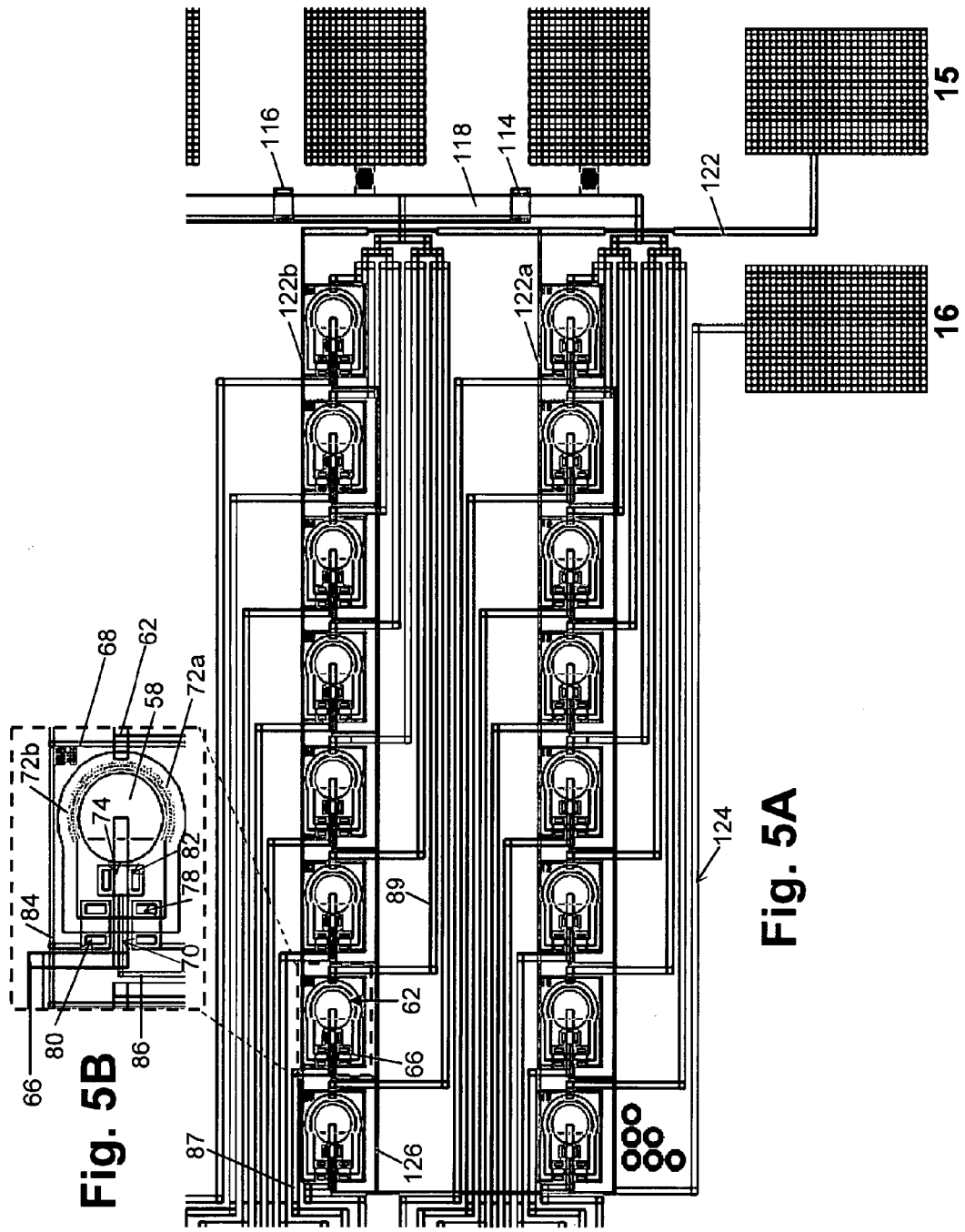

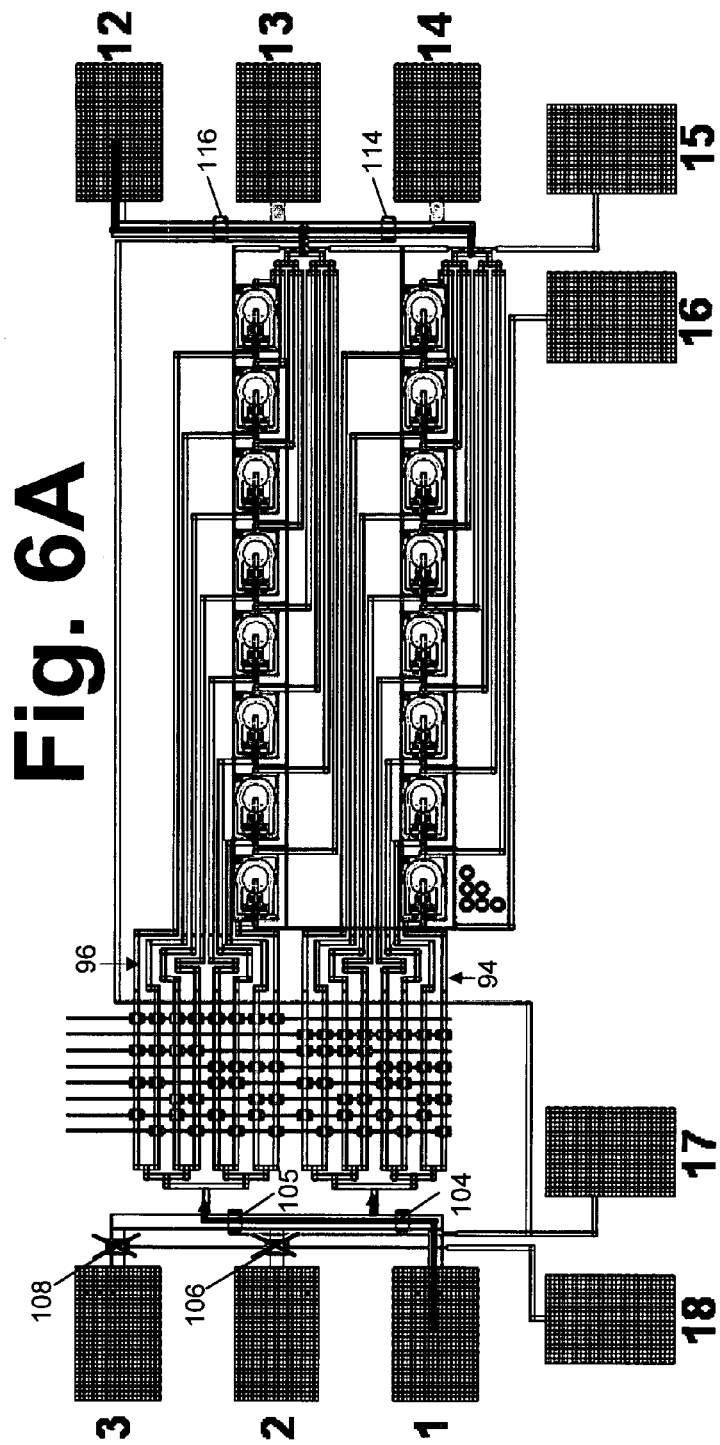

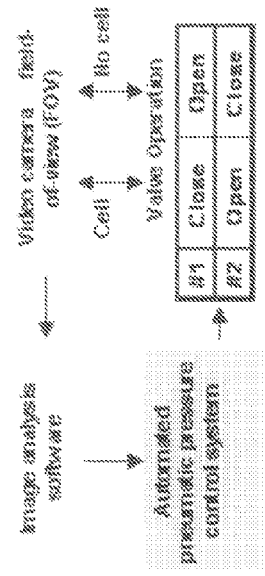
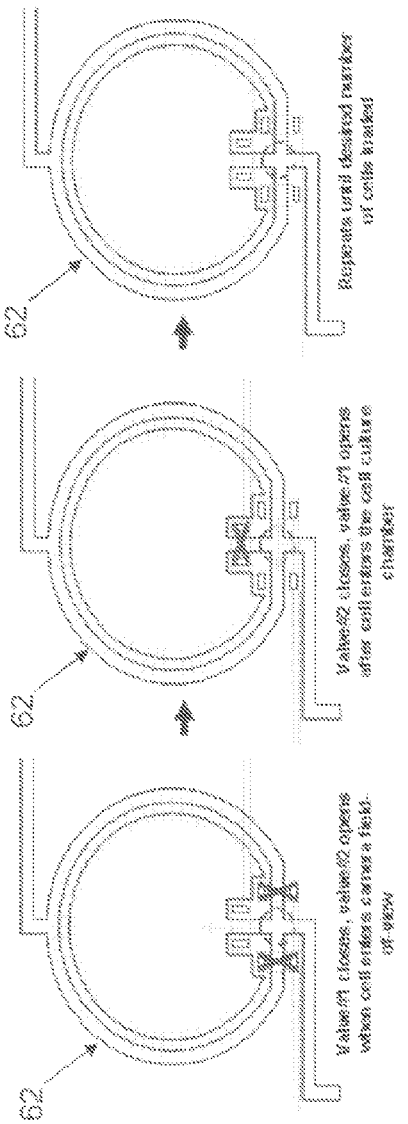
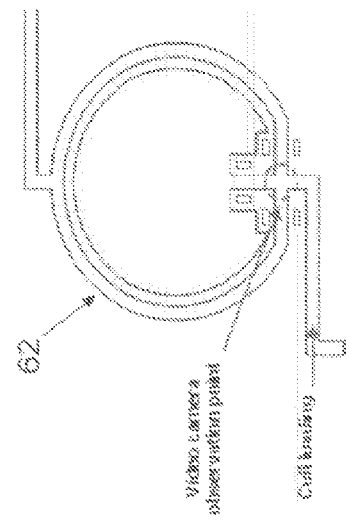

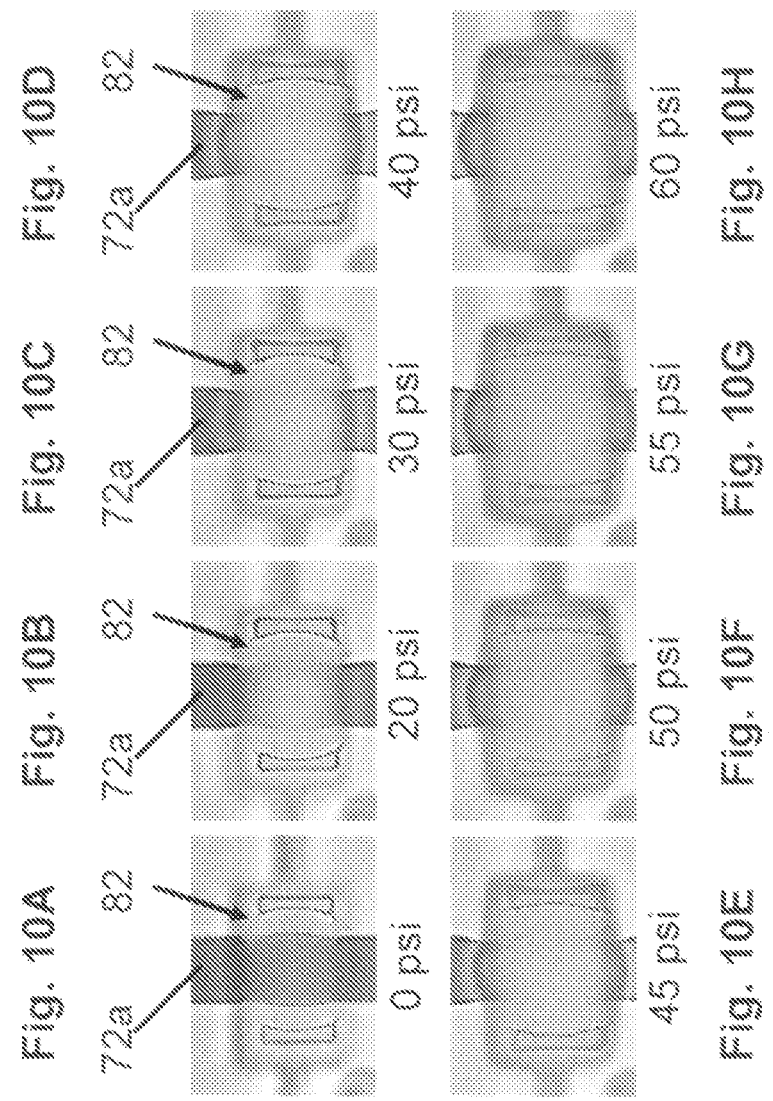

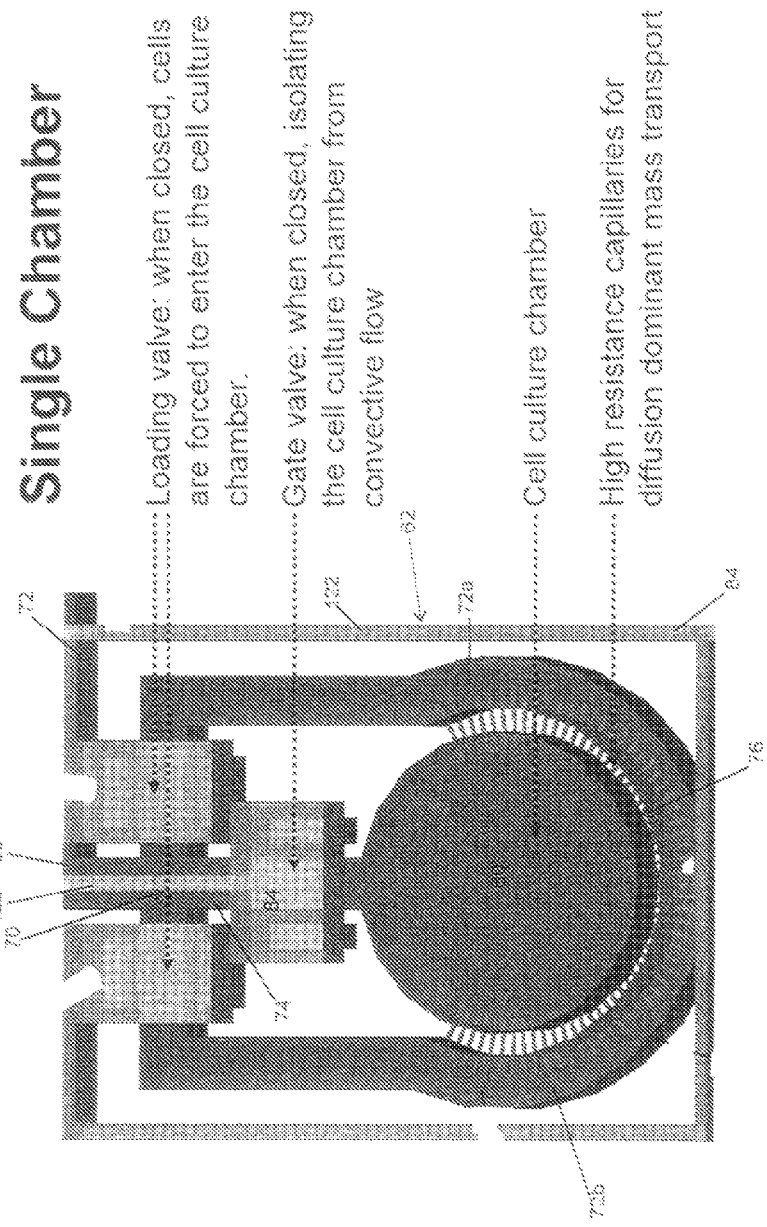

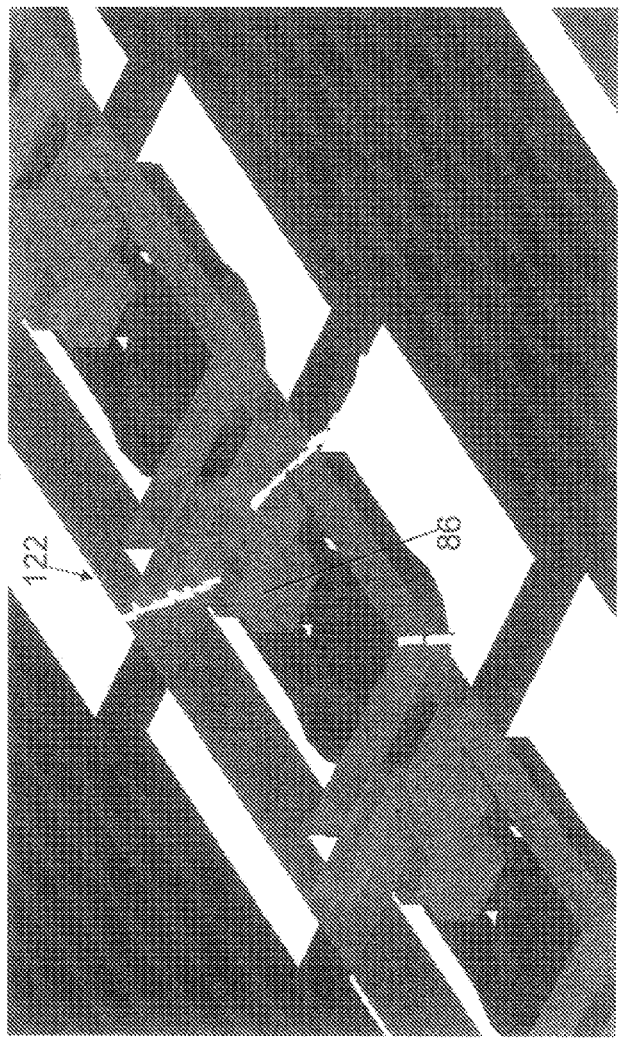

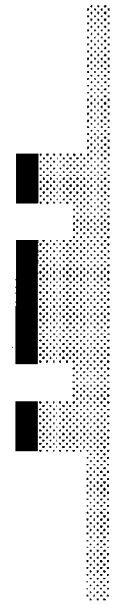
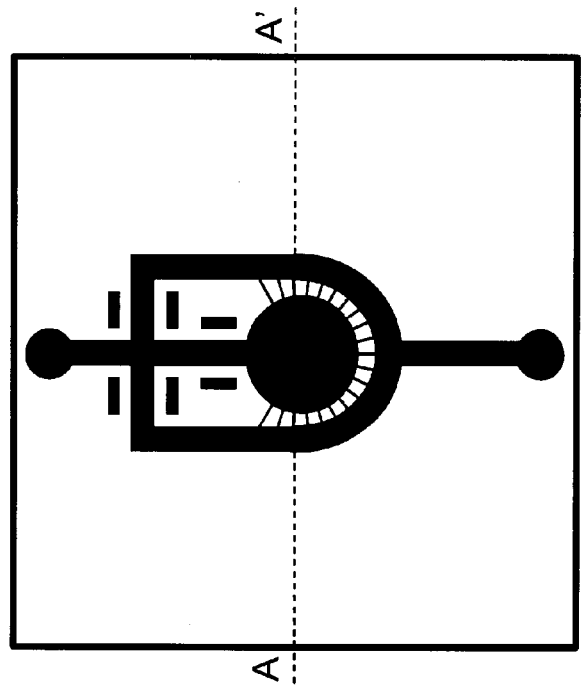
Fig. 13F

Fig. 13H
Plan View
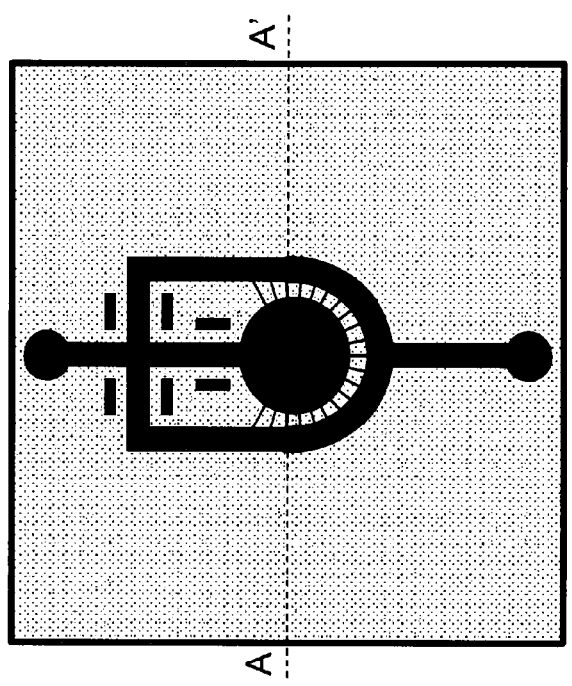
A-A' Cross Section

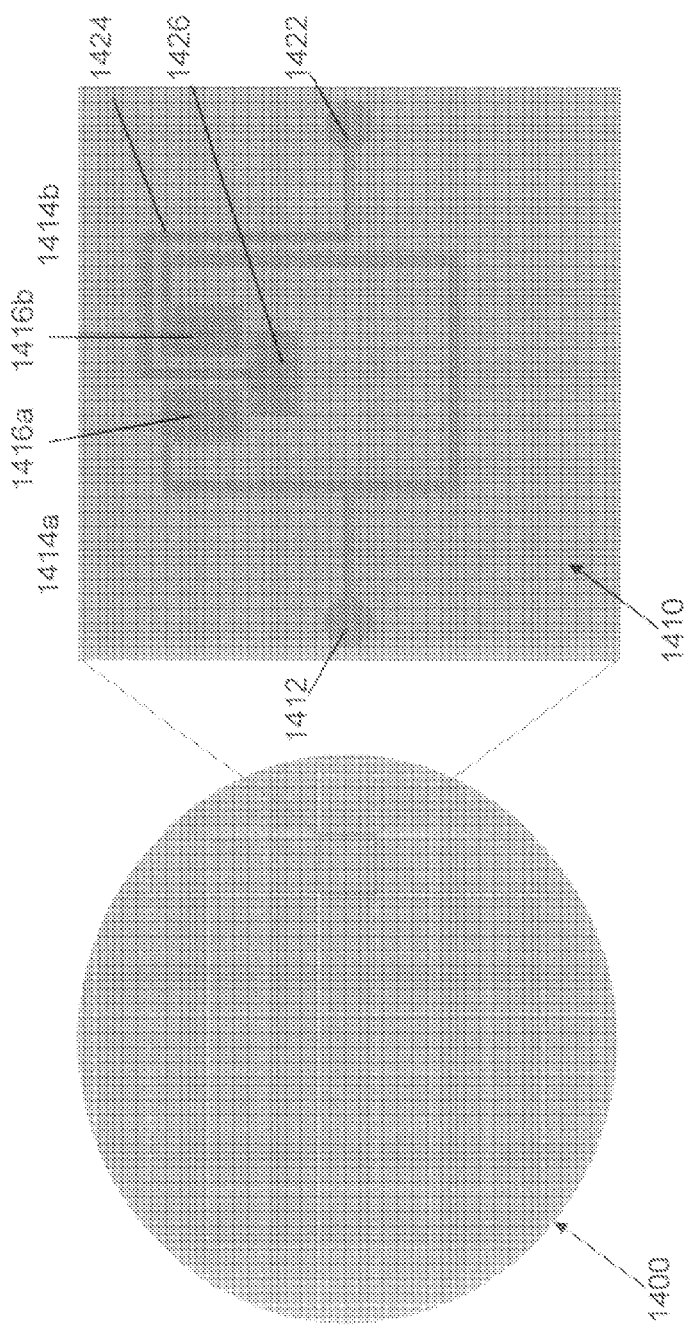

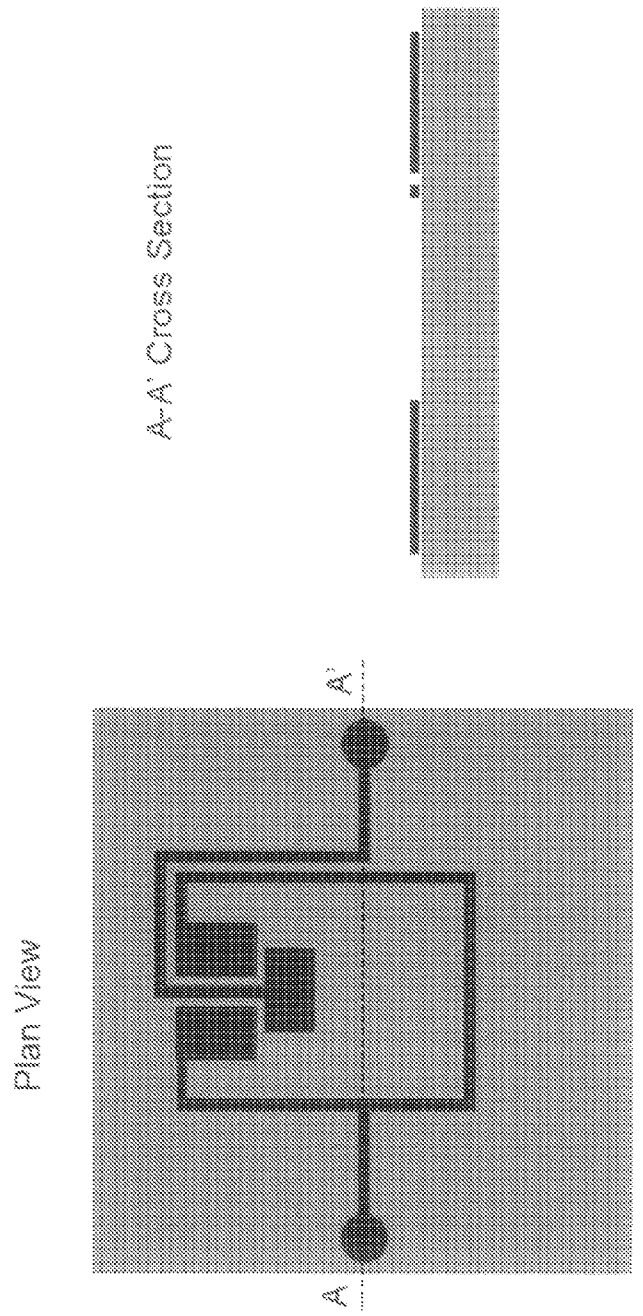

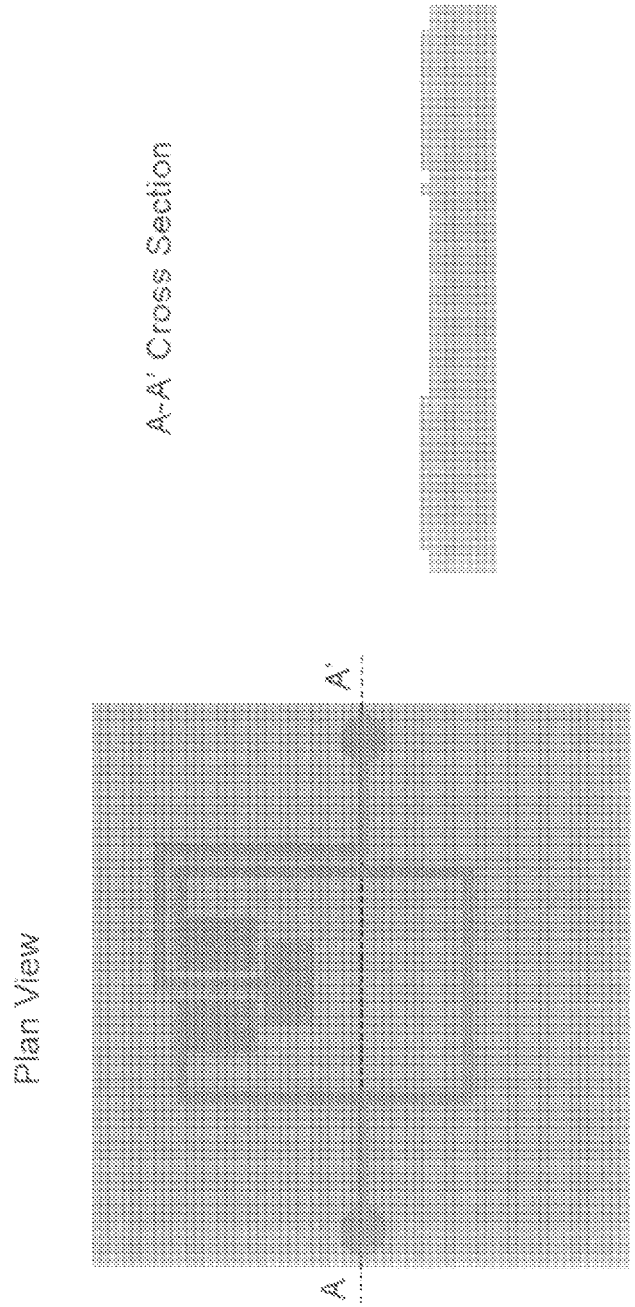

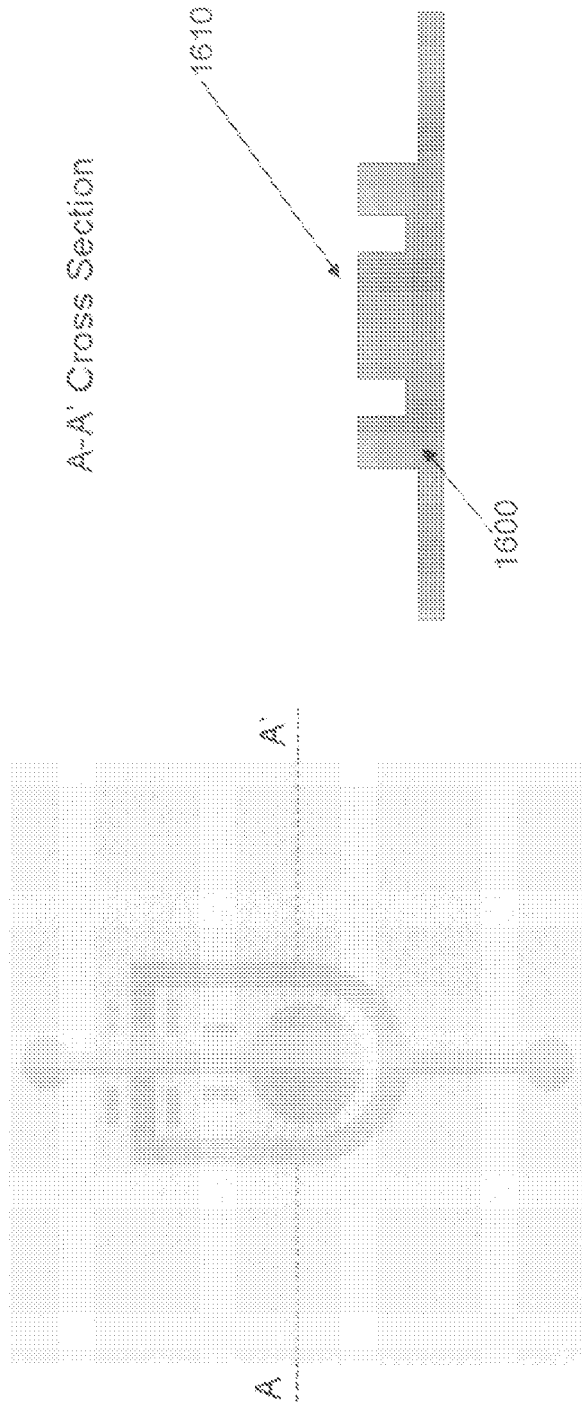

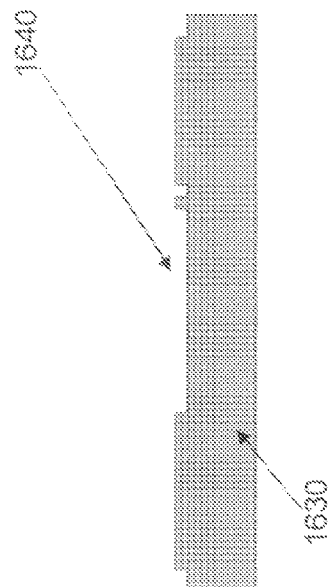
Fig. 16C
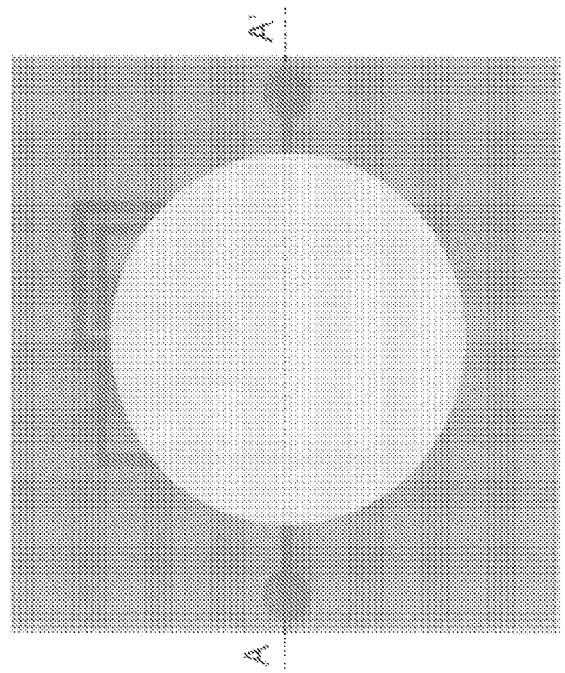

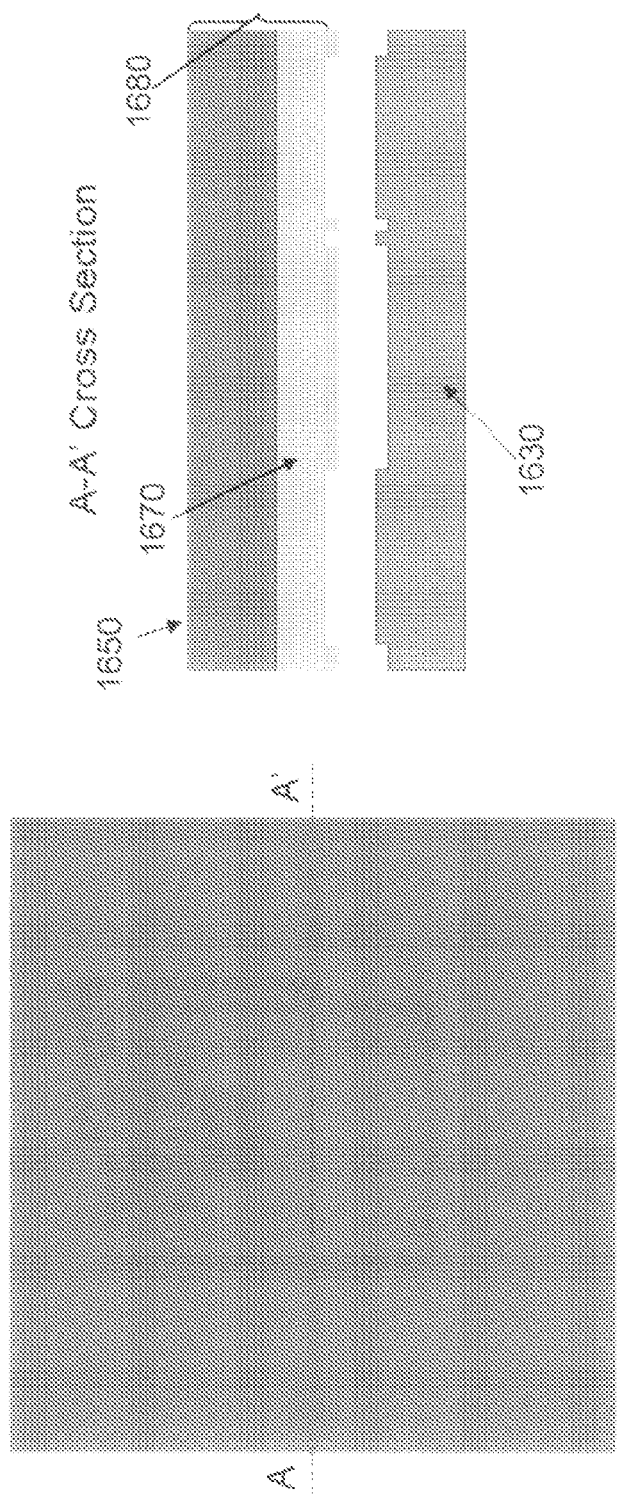

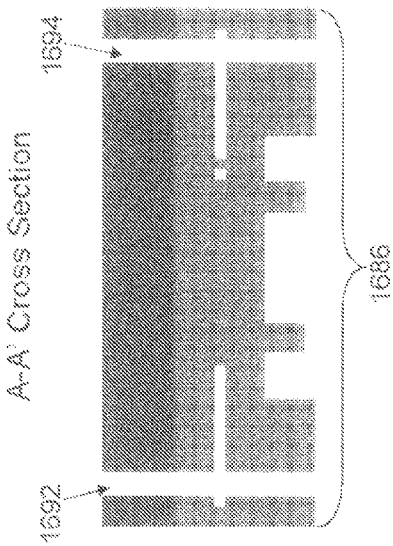
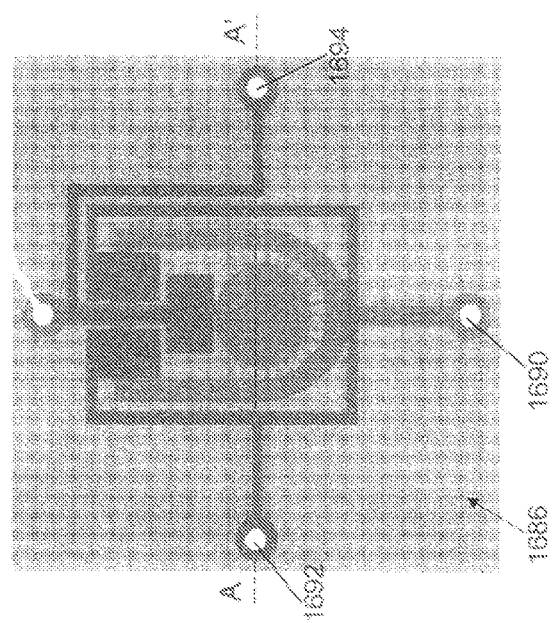
Fig. 16J

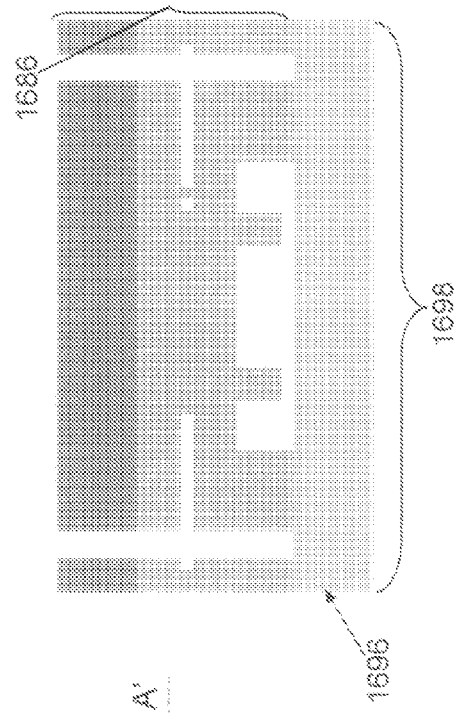
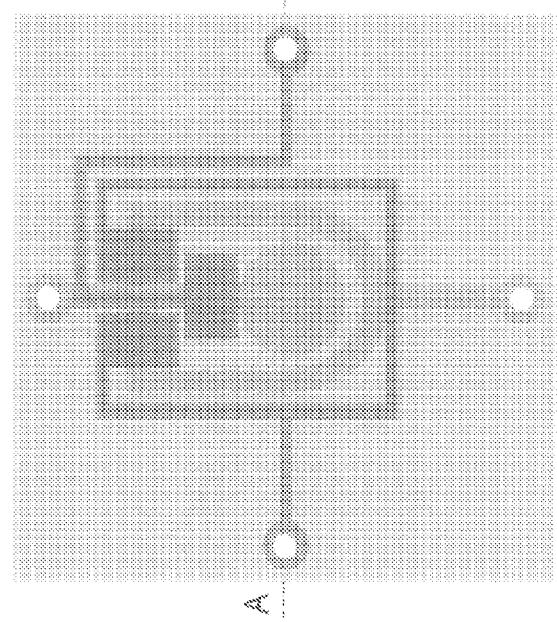
Fig. 16K

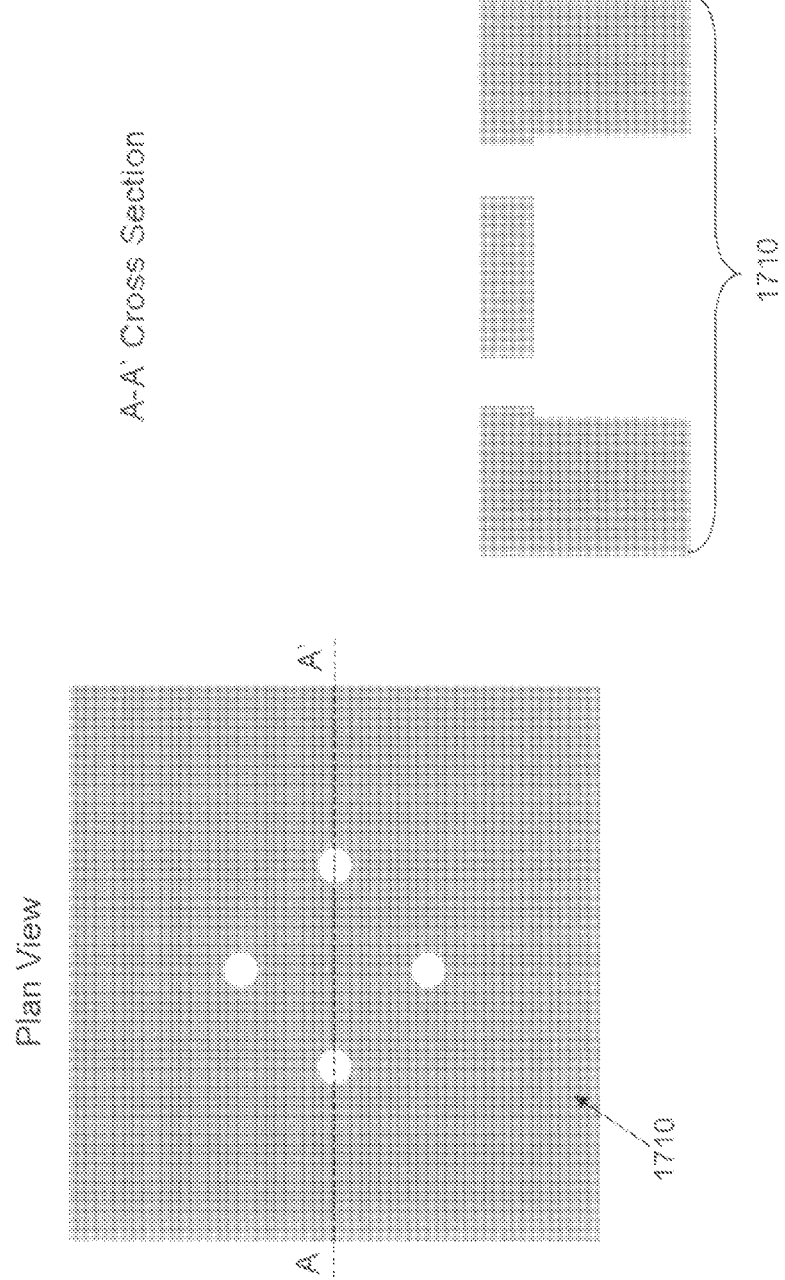

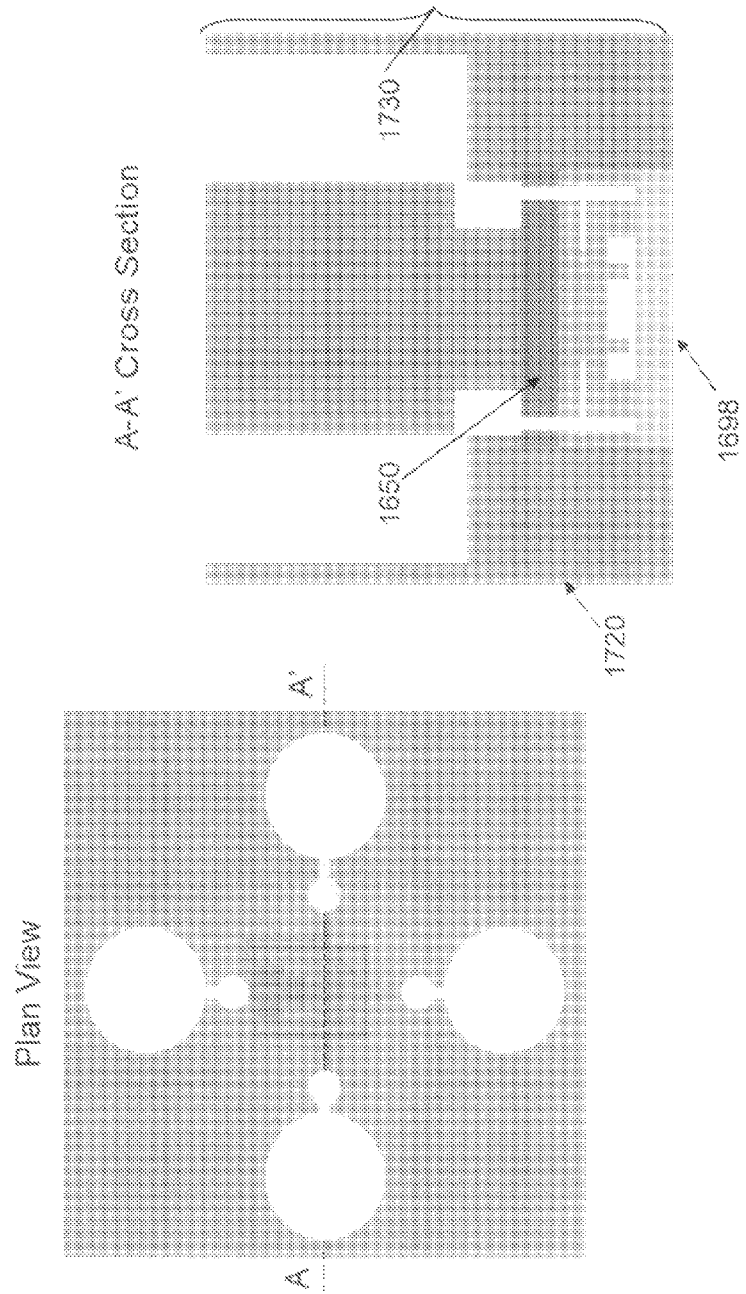

VALVED, MICROWELL CELL-CULTURE DEVICE AND METHOD

This patent application is a divisional application of U.S. patent application Ser. No. 11/648,207, filed Dec. 29, 2006, now U.S. Pat. No. 8,257,964 and claims priority to U.S. provisional patent application No. 60/756,399 filed on Jan. 4, 2006, which is incorporated in its entirety herein by reference.

FIELD OF THE INVENTION

The present invention relates to a microwell device and method, and in particular, to a valved microwell array device designed for high throughput cell culture assays, to microvalve for use in the device, and to methods for making the valve and device.

BACKGROUND OF THE INVENTION

There is a growing demand in the drug discovery and related fields for high throughput cell culture systems, that is, systems capable of supporting large numbers of cell-culture assays in parallel. For a variety of reasons, it would be desirable to conduct large-scale cell-culture assays in a microfluidics device having an array or microwells and microfluidics structure for populating and feeding the wells. One major advantage of microfluidic cell culture is the possibility to mimic in vivo conditions. Culture parameters such as medium flow rate, shear stress, Peclet number, Reynolds number, liquid/cell volume ratio, length scale, and cell density can be controlled to more closely match physiologic conditions. Continuous medium perfusion and "on-chip" monitoring ensure a stable environment for cells during observation. These factors should limit variations in cell behavior and improve the statistical power of experiments. It is also likely that by providing more in vivo-like culture conditions, cell behavior will be closer to physiologic conditions, making assay results more relevant for medical applications.

The potential advantages of a microwell array device have been realized to a rather limited extent only in the prior art. Various limitations associated with prior art devices include (i) the requirement for bulky robotics to populate the wells in the device, (ii) difficulty in preventing microfluidics structures from being blocked by cell growth within the structures, (iii) inability to sustain uniform culture conditions over an extended assay period, (iv) inability to achieve and alter cell-culture conditions at the level of individual wells, and (v) difficulty in creating the necessary microfluidics structures efficiently by microfabrication.

It would therefore be desirable to provide a microwell array device capable of more fully realizing the advantages noted above in a high throughput cell culture system. There is also a need to achieve these advantages in a microfluidics device that can be constructed efficiently by microfabrication.

SUMMARY OF THE INVENTION

In one aspect, the invention includes a valved microwell device composed of a substrate having formed therein, a microfluidics passageway having (i) a microwell for receiving particles, such as cells therein, (ii) an inlet channel segment, (iii) an outlet channel segment, (iv) a channel intersection segment having a first channel arm that communicates the inlet and outlet channel segments, and a second channel arm communicating the inlet channel segment with the interior of the well, where the first channel arm flows around a portion of the well, and (v) a porous barrier through which fluid, but not cells, in the well can perfuse from the well into the first arm.

A microvalve disposed in the second channel arm is operable to control the flow of fluid from the inlet channel segment into the well, such that a cell carried in a fluid moving through the inlet segment can be diverted into the well by opening the valve, and once diverted into the well, can be captured therein, with fluid flowing through the passageway, by closing the valve, and culture medium flowing through the first arm can exchange solute components with culture medium within the well by diffusion of such components across the porous barrier. The microvalve may have the construction described below.

The device may further include another microvalve disposed in the first channel arm, operable to control the flow of fluid from the inlet channel to the outlet channel. The first channel arm may have a pair of branches that flow around opposite sides of the well, and the other valve may include a pair of valves controlling fluid flow through each branch.

The device may include a plurality of such passageways, a microchannel well-distribution network for supplying input fluid to each of a selected one or more of wells in the passageways, under the control of a plurality of valves associated with the network, and first and second valve-supply networks for supplying fluid pressure to the first and second microvalves, respectively.

In still another aspect, the invention includes a microarray culture system, including a microarray device having a substrate, and formed in the substrate, a plurality of microfluidics passageways, each having (i) a well for receiving particles, such as cells therein, (ii) an inlet channel segment, (iii) an outlet channel segment, (iv) a channel intersection segment having a first channel arm that communicates the inlet and outlet channel segments, and a second channel arm communicating the inlet channel segment with the interior of the well, where the first channel arm flows around a portion of the well, and (v) a porous barrier through which fluid, but not cells, in the well can perfuse from the well into the first arm. Associated with each passageway is a first microvalve disposed in the first channel arm for controlling the flow of fluid from the inlet channel segment into the first channel arm, and a second microvalve disposed in the second channel arm for controlling the flow of fluid from the inlet channel segment into the passageway well.

A microchannel well-distribution network in the device is operable to supply input fluid to each of a selected one or more of wells in the passageways, under the control of a plurality of valves associated with the network, and first and second microchannel valve-supply networks are operable to supply fluid pressure to first and second valves in the passageways, respectively. A plurality of reservoirs is each in fluid communication with a channel in the well-distribution network or in the valve-supply network. A controller in the system operates for supplying pressurized fluid to selected ones of the reservoirs, thereby to supply fluid to a selected one or more of the microfluidic passageways and to selected valves.

In a system containing N passageways, the microchannel distribution network may have X separate valved channels, where $X = 2 \log_2 N$. The first and second valve-supply networks may operate to supply fluid pressure simultaneously to all of the first valves, and to all of the second valves, respectively.

The system may further include a detector by which the presence or absence of cells in a passageway intersection can be determined, and a controller for sequentially activating the second and first valves for capturing a cell in such intersection in the associated well.

The reservoirs in the system may have at least one cell reservoir for holding cells to be introduced into the passageways, and at least one reagent reservoir for holding a solution to be perfused through the passageways. The system may further include a sample-control network for controlling the flow of fluid in the cell and reagent reservoirs to the well-distribution network.

The controller may operate in one mode to open the first valve, and close the second valve in each passageway, so that a cell-culture medium contained in a reagent reservoir flowing from a device inlet to a device outlet can exchange solute components with cell culture medium in each well across the porous barrier.

The controller may operate in another to close the first valve, and open the second valve of in each passageway, so that a medium flowing from a device outlet to a device inlet will carry the cells in the device wells out of the device.

In another aspect, the invention includes a valved microfluidics device having a substrate, a microchannel through which liquid can be moved from one station to another within the device, and a pneumatic microvalve adapted to be switched between open and closed states to control the flow of fluid through a microchannel. The microchannel is formed of (i) two or more flexible membranes forming wall portions in a valved region of the microchannel, including a primary membrane and one or more secondary membranes that are each joined to the primary membrane at a common edge, and (ii) a chamber formed in the substrate, separated from the microchannel by the primary membrane and adapted to receive a positive or negative fluid pressure, thus to deform the primary membrane. Deformation of the primary membrane causes the secondary membrane(s) to deform, and the combined deformation of the primary and secondary membranes is effective to switch the condition of the valve between its open and closed states.

The device may include, for each secondary membrane, a recess formed in the substrate into which the secondary membrane is deflected when deformed. The flexible membranes may include a top-wall primary membrane and a pair of opposite side-wall secondary membranes, with the valved region of the microchannel, with the valve in its open state, being substantially rectangular. The height to width ratio of the rectangular microchannel may be at least about 0.5 to 1.0. The application of positive pressure to the chamber, to place the valve in its closed state, may cause the primary membrane to bow outwardly into the channel, and the secondary membranes to bend outwardly at their common edges with the primary membrane, into the associated recesses, thus to enhance the extent of sealing between the primary membrane and the two secondary membranes as the primary membrane is deformed.

The flexible membranes in the device may be formed of any elastomer that is compatible with microfabrication techniques, e.g., PDMS elastomer.

The microchannel in the device may intersect a channel segment, and the valve may be positioned in the channel segment to control the amount of fluid flow from the microchannel into the segment. The channel segment may connect the microchannel with a well formed in the substrate, where the valve is used to control the flow of fluid from the microchannel into the well.

In a related aspect, the invention includes a microfluidic device comprising an elastomeric monolith situated between a rigid substrate and a semi-rigid substrate. In one embodiment the two substrates are planar. In another embodiment the elastomeric body comprises multiple elastomeric layers separately prepared and having defined in a first surface of each layer a pattern of channels and/or chambers. The separate layers are bonded together to form the monolith such that the microfluidic features (e.g. channels, chambers, etc.) defined in the surface of one layer are sealed off against the surface that lacks microfluidic features of a different layer. Preferably, the different layers contain features that operate in conjunction with those of another layer. When bonding the layers, the features of each layer are aligned such that they operate in conjunction with one another. Preferably, an adhesion promoter is used to bond the semi-rigid substrate to the elastomeric monolith.

In one embodiment the microfluidic device is prepared by combining a first elastomeric layer having microfluidic channels in a first surface and a second elastomeric layer having pneumatic control chambers in a first surface to form an elastomeric monolith. The monolith is characterized by having microfluidic channels disposed in a first surface and pneumatic control chambers disposed within the body of the monolith. Access holes providing communication from the external world to the channels and chambers are also provided through both of the substrates and the monolith.

In yet another aspect, the invention includes a method for fabricating a valved microfluidics device of the type described above. The method includes, in part, the steps of preparing a mold having a fluorocarbon surface coating, dispensing an elastomeric precursor over the coated mold; at least partially curing the elastomeric precursor and removing the at least partially cured elastomer from the mold. The method also further includes, in part, placing the side of a semi-rigid sheet coated with an adhesion promoter on top of the elastomeric precursor prior to the step of at least partially curing the elastomer, and after the curing step, removing the joined semi-rigid sheet and elastomer from the mold.

In one embodiment of a method for fabrication of a multi-layer microfluidic device, two molded elastomeric layers are formed, joined together and bonded to a substrate. A first mold is prepared having an upper layer fluidic design, and a second mold is prepared having a lower layer fluidic design. Preferably, the molds have a fluorocarbon surface coating. After an elastomer precursor is dispensed over the first and the second molds, the side of a semi-rigid sheet coated with an adhesion promoter is placed on top of the elastomer precursor spread on the first mold. The elastomer precursors are at least partially cured. Thereafter the joined semi-rigid sheet/elastomer unit is removed from the first mold, and the molded surface of the unit is placed over and aligned with the elastomer residing on the second mold. The two elastomer surfaces are bonded together, and the elastomers are fully cured during or following bonding. Thereafter the bonded elastomer assembly is removed from the second mold. The molded surface of the lower layer is bonded to a rigid substrate, thereby enclosing the features of the molded surface of the lower layer.

In yet another aspect, the invention includes a method of fabricating a microfluidic device comprising (a) an elastomer monolith and (b) a holder for both securing the monolith and providing ports for addressing the fluidic features of the monolith with external fluids and/or removing fluids from the monolith. The fabrication method comprises preparing (a) preparing a module comprising an elastomeric monolith having on one face a semi-rigid thermoplastic substrate adhered thereto, with ports through the semi-rigid substrate accessing a microfluidic network formed in the elastomeric monolith, (b) preparing a holder having on a first surface at least two recessed openings and having on the opposite surface a cavity, and openings within the cavity communicating with each of the recessed openings, and (c) bonding the semi-rigid substrate of the module within the cavity such that the ports of the module align with the openings in the cavity.

These and other objects and features of the invention will become more fully understood when the following detailed description of the invention is read in conjunction with the accompanying drawings.

BRIEF DESCRIPTION OF THE FIGURES

FIG. 4 shows the truth table for the microchannel well-distribution network in the device of FIG. 3;

FIGS. 5A and 5B show microvalve channel connections to the well device of FIG. 3 (5A) and an enlarged view of a single well and associated microvalves in the device;

FIGS. 6A and 6B illustrate of valve configuration of the FIG. 3 device when cells are to be supplied to the wells in the device (6A), and when the cells are being directed to a specific well (6B);

FIGS. 7A-7E illustrate valve-switching steps employed in capturing a cell in a well in the device, during cell loading to achieve selected numbers of cells in each well (7A-7D) and components of an automated cell loading assembly in the system;

FIG. 10A-10H illustrate the condition of a microvalve such as shown in FIG. 9 with increasing fluid pressure applied to the valve;

FIG. 11 is a three-dimensional perspective view of a single well and associated microvalves constructed in accordance with the invention, and having the layout of the passageway seen in plan view in FIG. 5B;

FIG. 12 is a three-dimensional perspective view of a three well and associated microvalves and channel connections in the device of the invention;

FIGS. 13A-13H illustrate successive steps for fabricating a mold useful for making a well, channels and valve region in a microfluidic layer of the microfluidic device of the invention;

FIGS. 14A-14E illustrate successive steps for fabricating a mold useful for making pneumatic chambers in a control layer of the microfluidic device of the invention;

FIGS. 16A-16K illustrate successive steps used to fabricate the microfluidic device of the invention; and FIGS. 17A-17D illustrate successive steps for preparing a device holder and an integrated microfluidic device/holder.

DETAILED DESCRIPTION OF THE INVENTION

A. Definitions

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microwell" refers to a micro-scale chamber able to accommodate a plurality of particles. A microwell is typically cylindrical in shape and has diameter and depth dimensions in a preferred embodiment of between 100 and 1500 microns, and 10 and 500 microns, respectively. When used to refer to a microwell within the microwell array device of the invention, the term "well" and "microwell" are used interchangeably.

A "microchannel" refers to a micron-scale channel used for connecting a station in the device of the invention with a microwell, or a station and a valve associated with the microwell. A microchannel typically has a rectangular, e.g., square cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably.

A "microfluidics device" refers to a device having various station or wells connected by micron-scale microchannels in which fluids will exhibit microfluidic behavior in their flow through the channels.

A "microvalve" refers to a valve operable to open and close a microchannel to fluid flow therethrough. When used to refer to a microvalve within the microwell array device of the invention, the term "microvalve" and "valve" are used interchangeably.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

B. Microarray Culture System and Device

Figure 1:
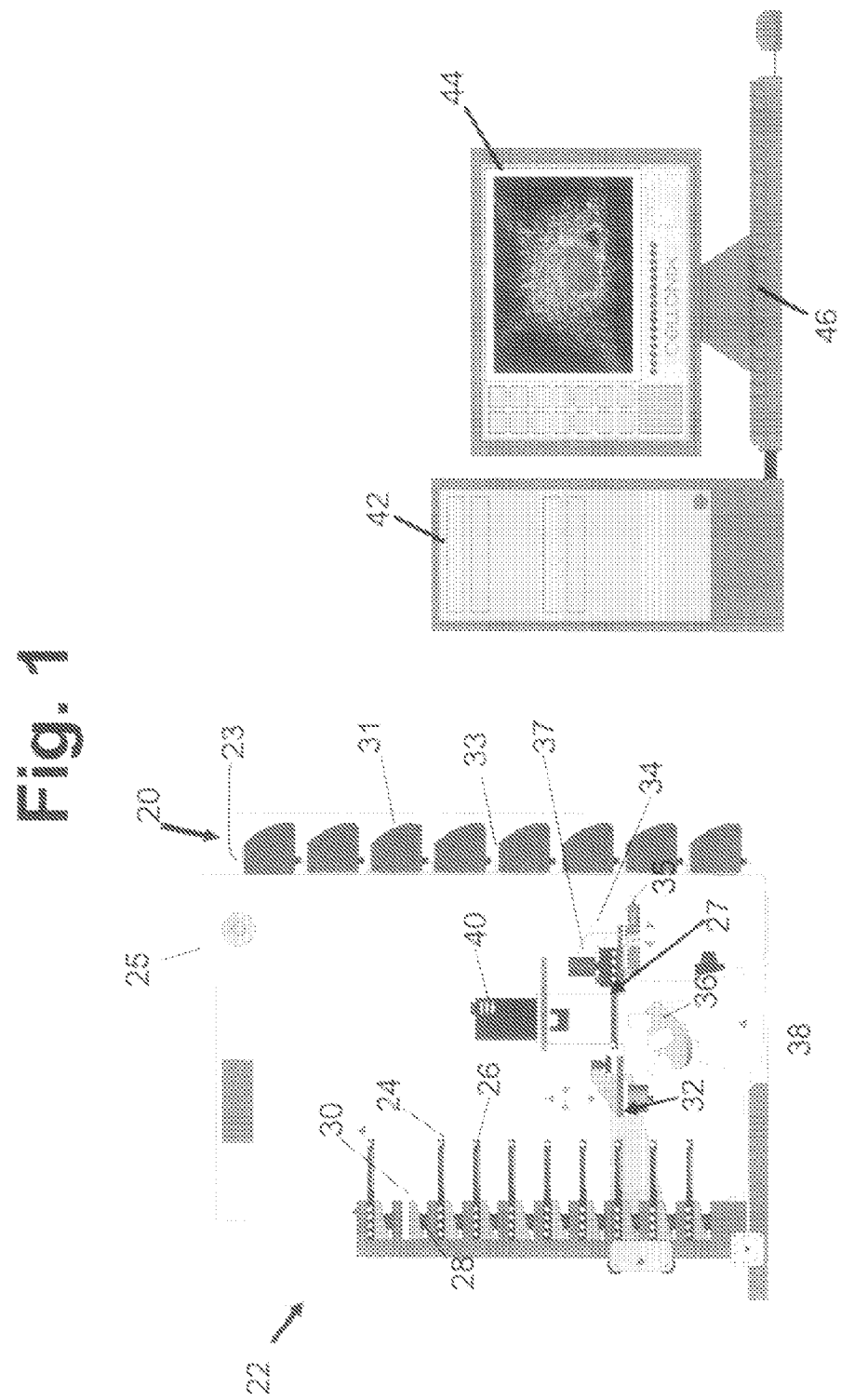
FIG. 1 shows a microarray cell culture system employing multiple microwell array devices constructed in accordance with the invention.

FIG. 1 shows a microwell array system 20 in accordance with one aspect of the invention, for conducting cell-culture assays, and more generally, for conducting assays involving particles such as cells, viruses, liposomes, etc. in a culture environment. System 20 includes a chamber 22 for holding a plurality of plates, such as plates 24, 26, which will be described below with respect to FIG. 2. These plates are carried on a cell-culture tower 28 having a plurality of plate slots, such as slot 30, for releasably holding individual plates. Each slot provides a plurality of fluid pressure connections (not shown) between reservoirs in each plate and system solenoids, such as solenoids 31,33, which can be activated to supplied pressurized fluid, such as air at 500 kPa pressure, to the respective reservoirs in the plates supported in each slot. In the embodiment that will be illustrated herein, the microarray device in each plate contains an 8×2 array of microwells, and is serviced by a total of 18 reservoirs per plate. The system thus contains 18 individually controllable solenoids, where each solenoid will supply pressure to a 10-outlet manifold that connects that solenoid to a designated reservoir in each of the 10 plates.

A robotic arm 32 in the system is vertically shiftable on the tower to positions at which the arm can engage a selected plate, such as plate 27, remove the plate from its slot, rotate the engaged plate 180°, and vertically move the plate for placement on a horizontally movable x-y stage 35 of a loading and observation structure 34 in the chamber. When a plate is removed from a slot, and thus disconnected from the pressure supply lines from the solenoids, it may be connected to a manifold coupler 37 which couples the plate reservoirs to the respective solenoids, allowing activation of various valving functions used for loading cells into the microwell array device carried on the plate, when the plate is positioned on structure 34, as will be described below.

Structure 34 includes a microscope 36, camera 38, and an optical detector 40 for sensing the position of cells at selected locations on a microwell array chip supported on the plate, as will be described. As noted above, stage 35 is movable, in small x-y increments within the filed of the microscope, to position the chip carried on the plate at selected located within the field of view of the microscope.

Culture conditions within the chamber are maintained by air- and CO2-supply to the chamber and by heaters (not shown) within the chamber.

Also included in the system is a computer or processor 42, and keyboard 46 and monitor 44 for user input and program display. The computer is operatively connected to the detector and to the solenoids, such as solenoids 31, 33 for controlling gas pressure to the plate manifolds in accordance with the cell-loading and cell-culturing operations performed by the system, to be described below.

Figure 2:
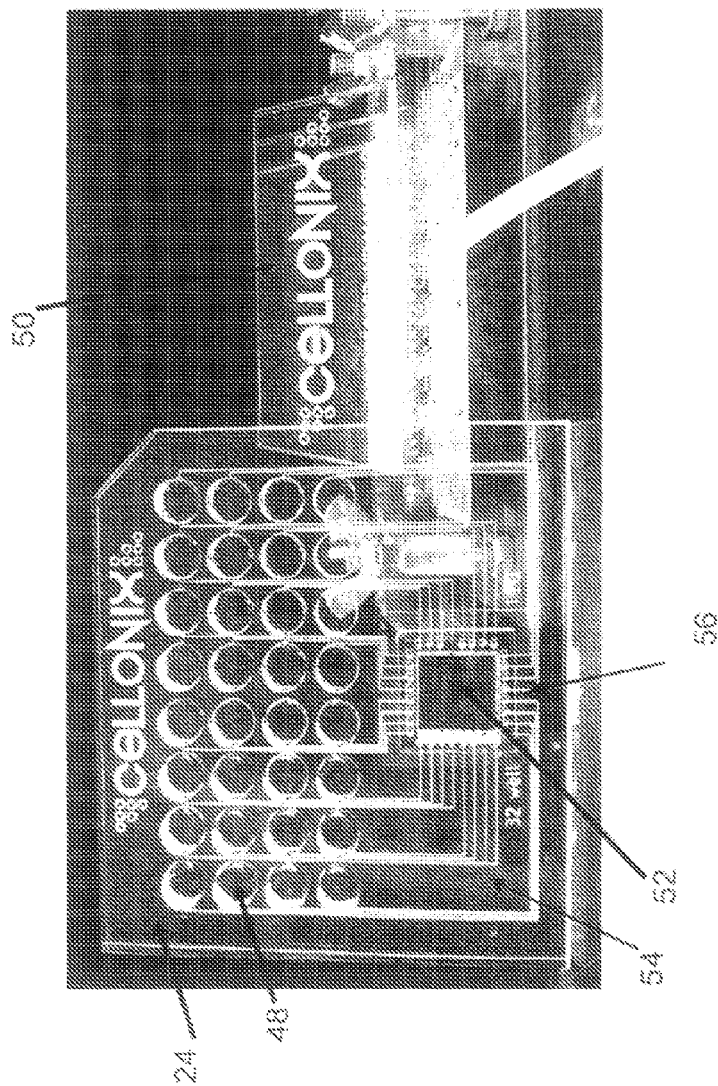
FIG. 2 shows one of the cell-culture array plates in the system of FIG. 1 and the reservoir connections to the microarray device on the plate.

FIG. 2 shows a plate, such as plate 24, for carrying out multiple cell-culture assays in parallel, in accordance with one aspect of the invention. The plate illustrated supports a microarray device or chip 52 having an array of microwells, microchannels, microvalves, and port stations, as will be described. Control of various media supplied to the microwells, and microvalves, during a cell loading and culture assay, requires a plurality of reservoirs, such as reservoirs 48, 50, containing fluid which is delivered to a corresponding number of input stations on the chip. The chip illustrated in FIGS. 2-6 has an 8×2 array of microwells, and is supplied by 18 reservoirs on plate 24. Each reservoir is connected to a corresponding port station in the chip by a channel, such as channels 54, 56 formed on the plate.

In operation, the reservoirs in a plate are covered by a leak-tight gasket (not shown) that serves as a manifold between the system solenoids and each plate. That is, the gasket contains a line for pressurized gas between each solenoid manifold and one of the reservoirs on the pressurized-gas line.

Figure 3:
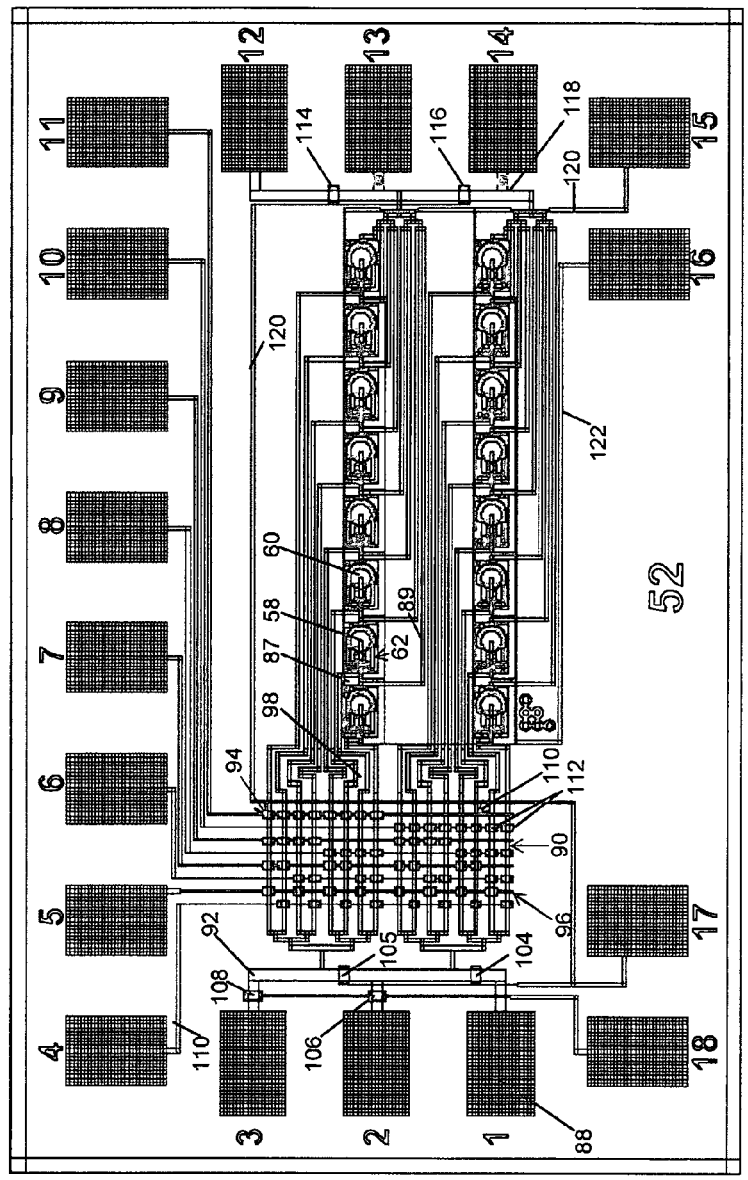
FIG. 3 shows a plan view of a microarray cell culture device having an 8×2 well array, and channel connections to 18 reservoirs.

FIG. 3 shows the arrangement of microfluidic channels, well, and valves in an 8×2 microwell array device 52 constructed according of an embodiment of the invention. The device shown contains an 8×2 array of microwells, such as microwells 58, 60, where each microwell is part of a passageway, such as passageway 62 containing microwell 58. The layout and operation of passageway 62 is described below with respect to FIG. 5B. The chip is formed, in accordance with one aspect of the invention, by microfabricating the well, channel, and valve components on a substrate 64 as will be detailed in Section D below.

Passageway 62 in the device, which is representative, is illustrated in enlarged layout view in FIG. 5B. The microwell 58 in the passageway serves as one of the array of cell-culture microchambers in the device, and is supplied by an inlet segment 66 and drained by an outlet segment 68 in the passageway. Specifically, inlet segment 66 terminates at an intersection 70, at which media can be directed either around the well to segment 68 by a first 72 or second arm portion into the well, through a second arm 74. In the embodiment shown, the first arm includes a pair of first-arm portions 72a, 72b which bifurcate at intersection 70 and converge at outlet 68. The circumferential portion of the microwell that is bounded by arm portions 72a, 72b, is porous, or contains upper-ledge grooves, forming a barrier 76 effective to allow liquid in the well, but not cells, to flow into or out of the well from the two arm portions.

Also shown in FIG. 5B is a pair of first microvalves 78, 80 which control the flow of medium though arm portions 72a, 72b, respectively, and a second microvalve 82 which controls the flow of medium through second arm 74. The construction and operation of the microvalves will be detailed below in Section C. For purposes of the present discussion, it is only worth noting that the pair of second valves are activated by pressurized fluid supplied to the valves through a first microchannel valve-supply network, seen locally at 84 in FIG. 5B, and that the second valve is activated by pressurized fluid supplied to the valve through a second microchannel valve-supply network, seen locally at 86 in FIG. 5B. In operation, medium entering the passageway through inlet segment 66 may be directed into microwell 58 by closing first valves 78, 80, and opening first valve 82. This mode is used in directing and capturing cells in the microwell. Once a desired number of cells are contained in the well, the second valve is closed to capture the cells in the well, and the pair of first valves are opened to allow medium to flow through arm portion 72a, 72b, allowing exchange of medium components between the arm portions and the well. Finally, after an assay is completed, cells may be removed from the wells, by opening the second valve, closing the two first valves, and forcing medium through each passageway in an outlet-to-inlet direction.

As seen in FIG. 3 and FIG. 5A, the inlet segment in each passageway, such as inlet segment 66, is supplied by a microchannel, such as microchannel 87 that connects that passageway to a well-distribution network indicated generally at 90 in FIG. 3. The outlet segment of each passageway, such as segment 68 in passageway 62, is drained by a microchannel, such as microchannel 89, which feeds the passageway into an outlet channel 118. Thus, each group of eight passageways in the device is supplied by eight microchannels arrayed directly above the passageways, and each group is drained by eight microchannels, including microchannel 84 arrayed directly below each group.

With particular reference to FIG. 3, device 52 has 18 port stations, such as station 88, at which fluid from one of the eighteen reservoirs supplying the device is delivered to the individual passageways in the device or to the valves controlling the movement of medium through the passageways. These stations, which are numbered 1-18 in the figure, generally have the following supply or drain functions during chip operations. Stations 1-3 supply cells (station 1) or one of two different cell-culture media (stations 2-3) to each of the sixteen passageways. This supply is effected by a three-inlet supply-distribution channel 92, also referred to herein as a sample-supply network. From this channel, medium is directed to a selected passageway through the well-distribution network 90. As seen, the network has two sections 94, 96, each with eight microchannels, such as microchannel 98 in section 94, that are connected to one of eight passageways through a connecting microchannel, such as microchannel 87 in section 96 supplying passageway 62.

Flow of medium from one of the three supply-reservoir stations to the welldistribution network is controlled by a pair of microvalves 106, 108 activated by fluid supply from station 18, and a pair of valves 104, 105 activated by fluid supply from station 17.

Flow of medium through the well-distribution network is controlled by coordinated activation of each of eight valve sets controlled by fluid supply from stations 4-11. Each valve set, such as valve set 110, includes eight individual microvalves, such as microvalves 112, that are arranged on the sixteen channels of the network in a binary pattern seen in the truth table in Table 4. Columns 4-11 in this figure represent the eight valve-control stations, rows 1-16 represent the 16 passageways, indicated A1-H1 and A2-H2, and the unfilled blocks indicates a microvalve at that position row and column in the network. The pattern of filled blocks in the table indicates the pattern of closed valves that will direct medium to a selected one of the 16 passageways. As seen, each passageway can be uniquely accessed by closing some combination of four valves. For example, the microchannel supplying fluid to passageway H1 has four microvalves at positions corresponding to stations 5, 7, 9, and 11. Thus, closing valves 4, 6, 8, and 10 will leave this channel free for fluid flow, while blocking all others. Similarly, the microchannel supplying fluid to passageway HG has four microvalves at positions corresponding to stations 4, 7, 9, and 11. Thus, closing valves 5, 6, 8, and 10 will leave this channel free for fluid flow, while blocking all others. More generally, employing this binary-control scheme, an array of N microchannels can be individually accessed by X valve stations, each controlling N individual valves, where $X=2 \log_2 N$.

With continued reference to FIGS. 3 and 5A, reservoir stations 12-14 are stations through which media from one or more of the passageways are drained from the chip into a corresponding plate reservoir. The three stations are connected to a three-outlet channel 118 having two microvalves 114, 116 along its length as shown. These microvalves are controlled by fluid supply from station 17, through a microchannel 120.

Completing the description of the device layout, and with reference to FIG. 5A, the pair of first microvalves in each passageway, such as microvalves 78, 80 in passageway 62, is activated by fluid supply from station 15, which supplies pressurized fluid to each valve pair through a microchannel 122 that branches into two supply microchannels 122a, 122b. Thus supply of fluid pressure from station 15 is effective to close each of the 16 pairs of first microvalves in the device. Similarly, each of the 16 second microvalves in the device is activated simultaneously by pressurized fluid from station 16, which supplies fluid to each of the second valves through channels 124 and 126.

In a preferred embodiment, and as will be described more fully in Section C below, the device is preferably formed as a microfabricated silicon wafer, and has side dimensions of between about 50 to 150 cm. Each reservoir in plate 26 is designed to hold between about 0.001 and 0.5 cc of fluid, e.g., liquid, and each microwell typically holds 1 to 100 nl. The microwells and microchannels in the device have dimensions as indicated above.

The following setup will illustrate plate preparation, cell loading, and incubation operations carried out in the system. For this illustration, it is assumed that three different media will be supplied to the microwells: a suspension of cells used in loading cells into each of the 16 microwells through station 1, and cell-culture media solutions containing two different drugs or different concentration of the same drug, each of which will be supplied to one of the two groups of eight microwells (A1-H1 and A2-H2 in FIG. 4) through stations 2 and 3, respectively. These media are thus placed in reservoirs 1, 2, and 3 in plate 26 for delivery to the corresponding stations in the device. All of the other reservoirs, which will supply fluid to stations 4-18 are filled with a buffer solution. The device itself is placed on the plate so that its port stations are aligned to receive fluid from associated reservoirs on the plate, as shown in FIG. 2.

After filling the plate reservoirs with the above fluids, the reservoirs are covered and sealed with a gasket manifold that serves to connect each of the reservoirs to the associated solenoid valves. The plate is then moved to stage 35 in the system for loading each microwell in the device with cells. This loading procedure is carried out successively for each of the 16 microwells in the device. FIG. 6A illustrates the first valve setting required for cell loading. Here valves 104, 105 are in an open condition, and valves 106, 108 under the control of station 18 are placed in a closed condition. When the cell-suspension medium is applied under pressure to station 1, the cell suspension is forced toward each of the microchannel sections 94, 96, as indicated by the heavy fluid-path arrow in the figure. At the same time, valve 114, 116, are kept open to allow fluid in the passageways to be expelled through station 12 into the corresponding plate reservoir.

Figure 6B:
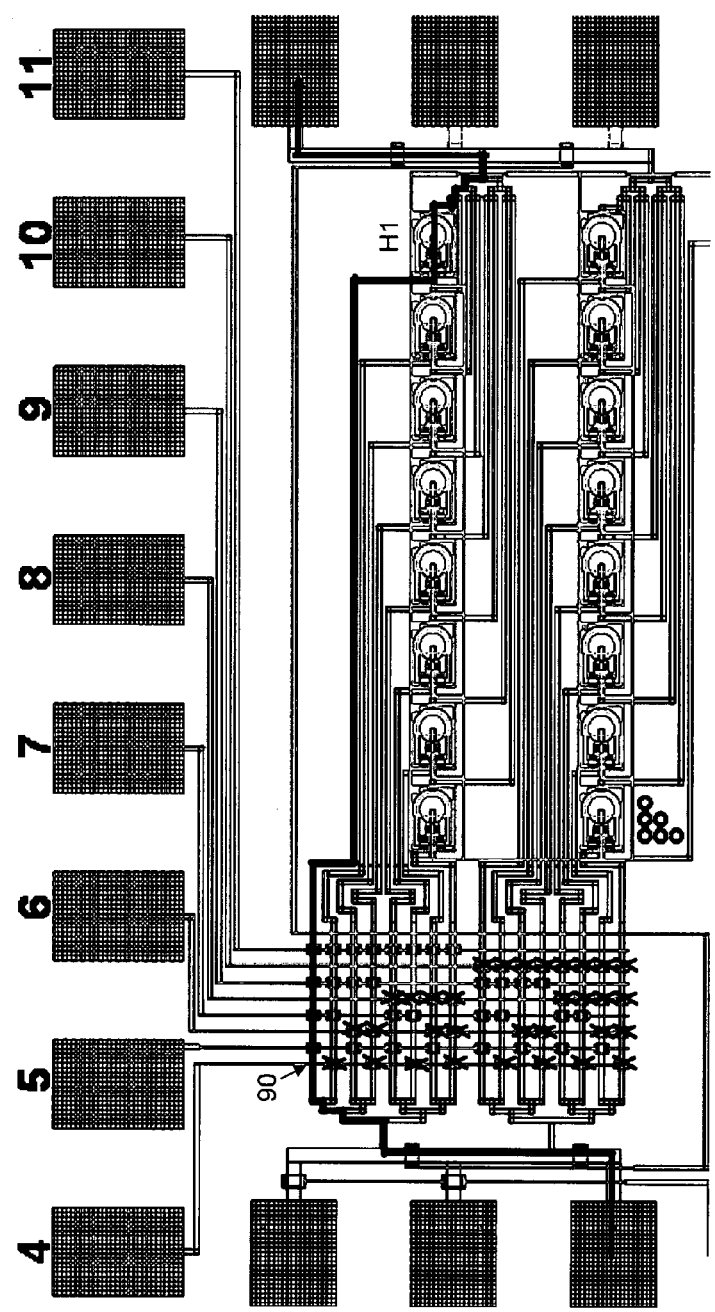
Figure 8:
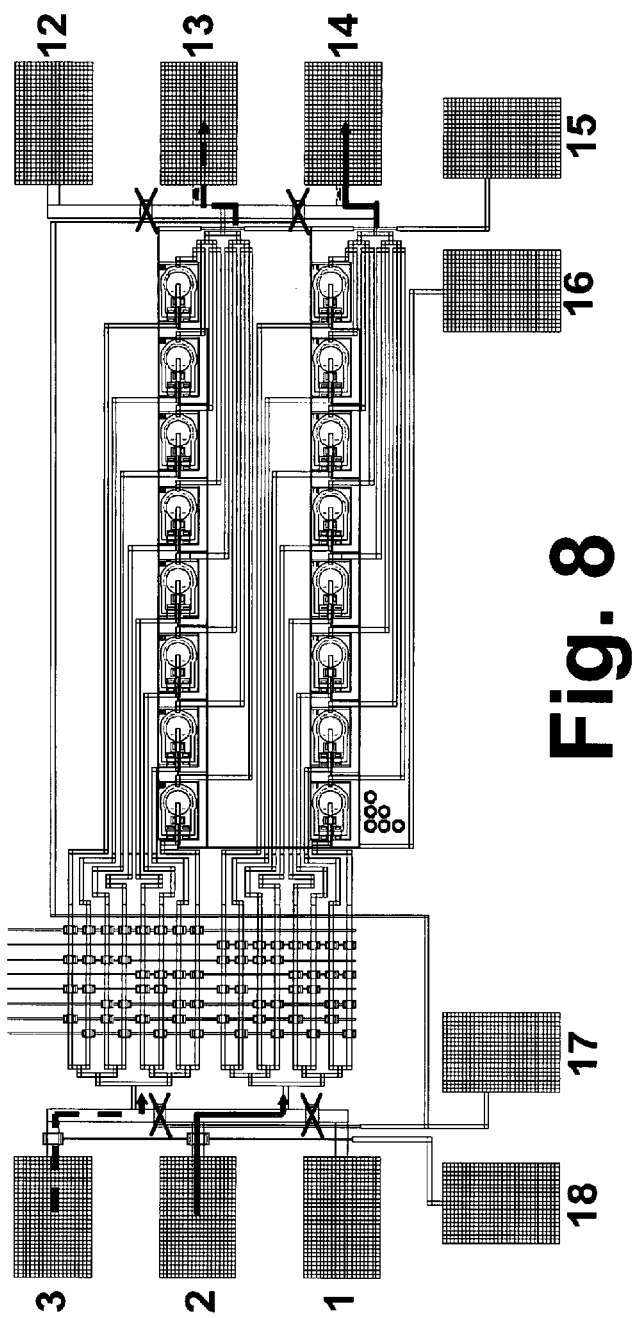
FIG. 8 shows the condition of certain valves in the device when two different drug solutions are perfused through wells 1-8 and 9-16, respectively, during a cell assay.
Figures 9A, 9B, 9C, 9D, 9E:
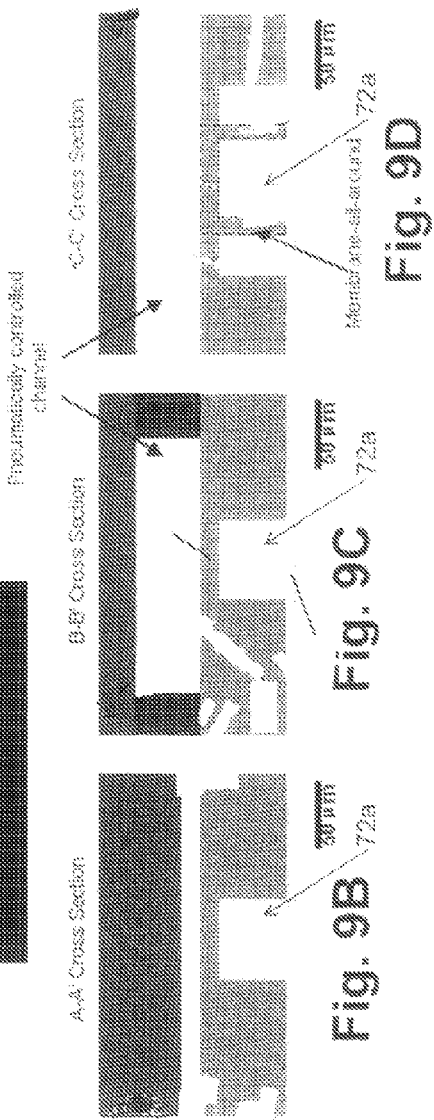
FIGS. 9A-9E are cross-sectional views of a microvalve device constructed in accordance with an embodiment of the invention, where 9D and 9E show the valve membranes in open and closed conditions, respectively.

The device is now in a condition for introducing cells into each of microwells. This is done, as indicated above, by selectively closing four of the eight sets of valves under the control of stations 4-11, to allow passage of fluid through the network to one passageway only. FIG. 6B illustrates the valve condition for supplying fluid through network 90 to the passageway designed H1. Here, the valve sets controlled by stations 4, 6, 8, and 10 are closed, blocking flow of fluid through all of the microchannels in the network except the top one in the figure connected the passageway H1. This valve configuration is maintained for a selected time and/or until a desired number of cells have entered and been captured in the selected microwell, as will now be described.

With continued reference to FIG. 6A, during the period that cells are being supplied to a selected microwell, the first and second microvalves controlling the movement of fluid in or around that well are controlled so as to achieve a desired number of cells in each well. In one embodiment, for introducing a selected number of cells in each well, cell loading is carried out on a cell-by-cell basis, as illustrated in the sequence of valve-control operation illustrated FIGS. 7A-7D. In these figures, a plate has been positioned on stage 35 in the system so that a selected microwell, e.g., microwell 58 in passageway 62 is within the optical field of microscope 36. At the initial stage of the sequence, seen in FIG. 7A, the first valves are open and the second valve is closed, forcing cell in the passageway to travel around rather than into the microwell. As a cell moves toward the intersection in the passageway, the first valves are closed and the second opened, as in FIG. 7B, allowing the single cell at the intersection to be carried into the microwell. Once the cell is within the well, the second valve is closed and the first valves opened, capturing the cell within the well while a second cell moves into a capture position at the intersection (FIG. 7C). This sequence is repeated until a desired number of cells have been captured in the selected microwell.

FIG. 6E shows components of the system control assembly for carrying out the above cell-loading operations in an automated fashion. The position of a cell in a microwell that is within the field-of-view of camera 38 in FIG. 1 is being viewed. Where it is desired to fill each well with an approximate, rather than precise number of cells, the above procedure can be simplified simply by opening the second valve and closing the first valves in a selected passage for a given period of time, during which all of the cells flowing through the passageway will be directed into and captured in associated microwell.

In the above-described operations, all of the pairs of first valves, and all of the second valves, are simultaneously activated from stations 15 and 16, respectively, as described above; thus, selective control of cells into any individual microwell is controlled at the level of the well-distribution network rather than by the valves controlling the movement of fluid within each passageway. This obviates the need for separate control over the valves in each passageway. Although the above cell-loading operations could be controlled by valving operations within each passageway, it will be appreciated that the well-distribution network offers a more efficient way of control fluid flow within each passageway. For example, in the present embodiment, controlling individual first and second valves in all 16 passageways would require 32 port stations rather than the 8+2 stations required with the configuration shown.

After loading each of the microwells with a selected number of cells, the device is switch to a cell-assay mode in which each of the microwells in the device are exposed to selected cell-culture assay conditions. As one example, assume it is desired to assay the cells the two groups of eight wells with two different concentrations of the same drug. Cell culture media containing each of the drug concentrations are then placed in the reservoirs feeding port stations 2 and 3 in FIG. 6A. By opening valves 106, 108 and closing vales 104, 105 in FIG. 6A, media from stations 2 and 3 are directed into the network sections 94, 96, respectively. With the all of the network valves maintained in an open condition, and with the first valves in the passageways maintained in an open condition, and the second valves in closed condition, medium from station 2 flows into each passageway, and around each microwell, exchanging medium components in each microwell across the porous barrier in each microwell. Over the course of the incubation period, the medium in the microwells remains substantially equilibrated with that inside the microwells, ensuring constant and uniform reaction conditions within the wells.

Also during the assay period, valves 114 and 116 are maintained in an open conditions, allowing material being forced through the passageways to be collected at the reservoir services by port station 12.

At the end of the cell-assay periods, e.g., after a 1-2 day incubation period, material from the two sets of microwells may be collected into each of two collection reservoirs through stations 13 and 14. As seen in FIG. 6A, switching valves 114 and 116 to their closed condition will divert media from the lower and upper sets of passageways, respectively, to stations 14 and 13, respectively, from which the material is collected in corresponding reservoirs 13, 14 on plate 24. The collected material may then be assayed conventionally, for example, for drug metabolic products or cell-secreted products.

Alternatively, where the cell assay involves inhibition or stimulation of cell growth, or uptake by the cells of a fluorescent material, the cells in the wells in each device may be inspected periodically, by removing a selected plate from tower 28 in FIG. 1, placing the plate on stage 35 for microscopic viewing, and individually inspecting the cells within each microwell.

C. Valved Microfluidics Device and Microvalve

This section will describe the construction and operation of a microvalve in accordance with one aspect of the invention, and a valved microfluidics device employing one or more such microvalves. The microvalve is suitable for use in the array device already described, and the microfluidics device may contain one or more valved microwell passageways of the type described above.

D. Microfabrication Methods

Figure 13A:
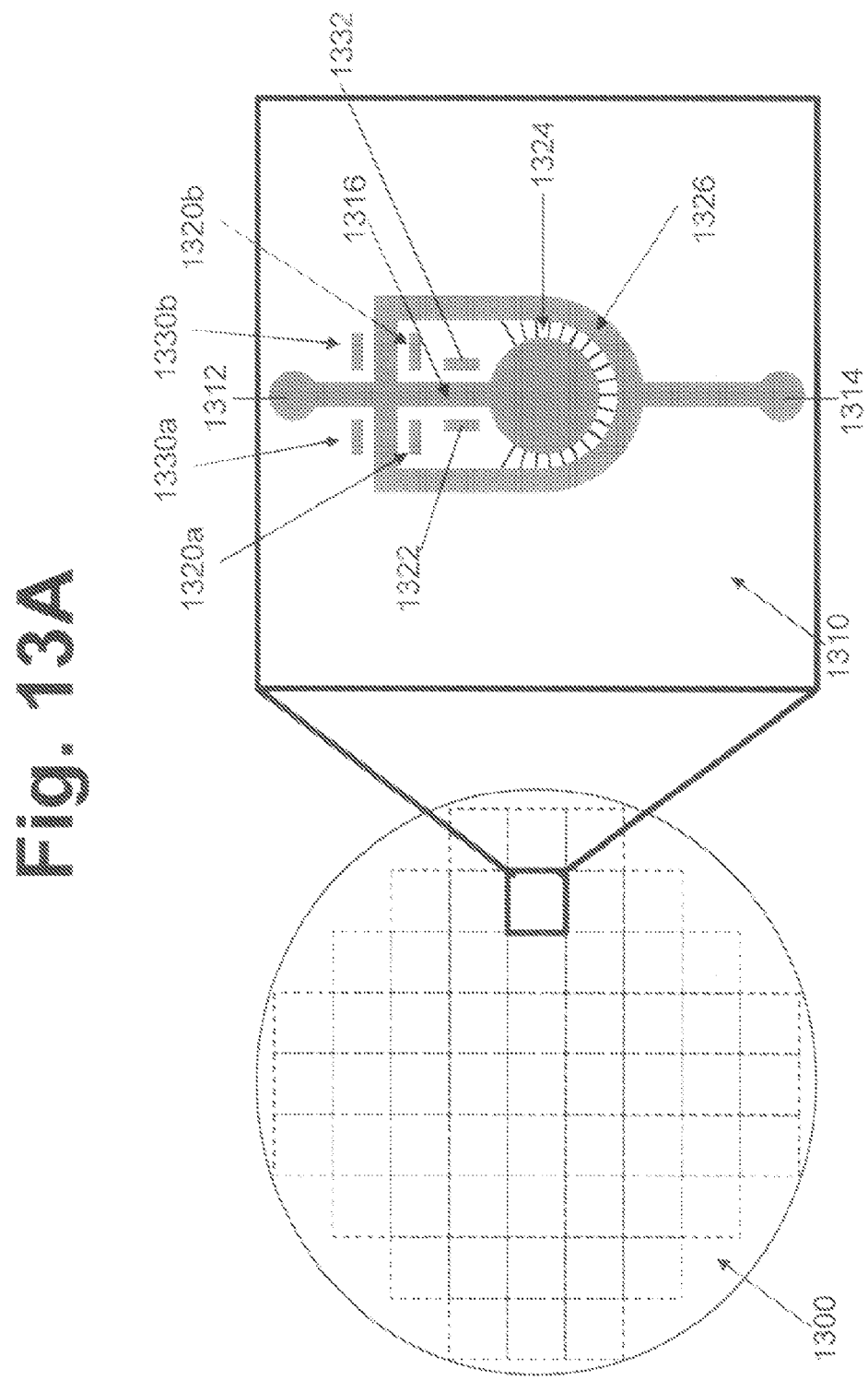
Figure 13B:
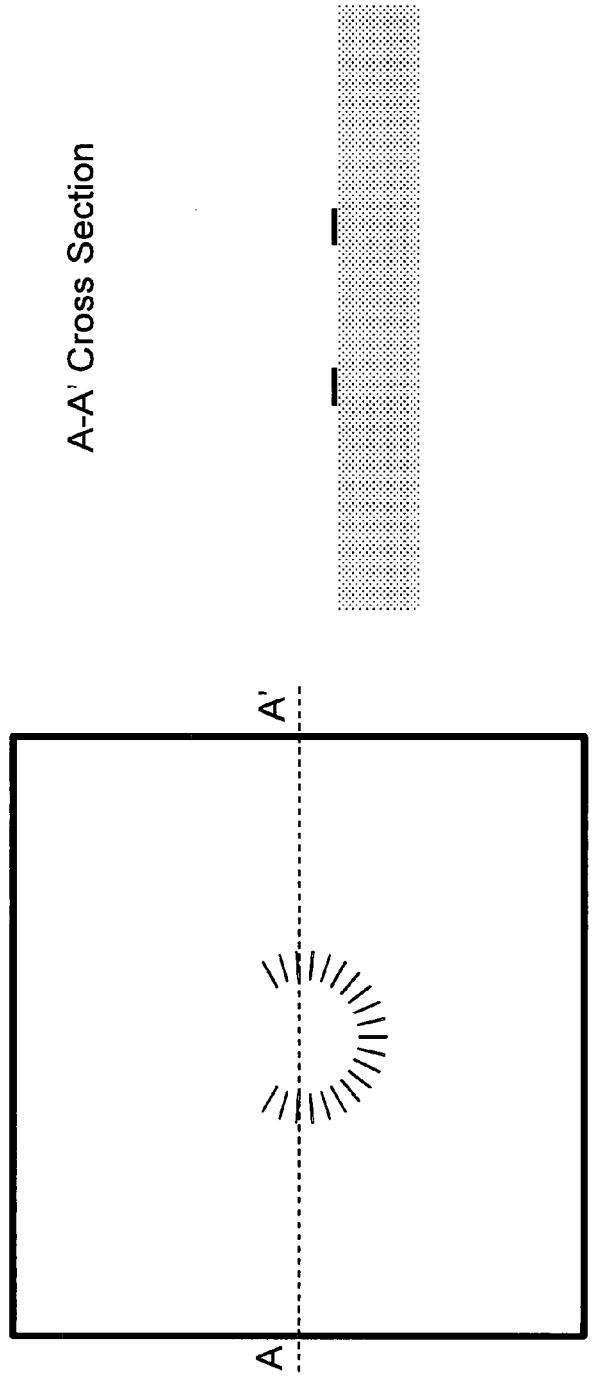
Figure 13C:
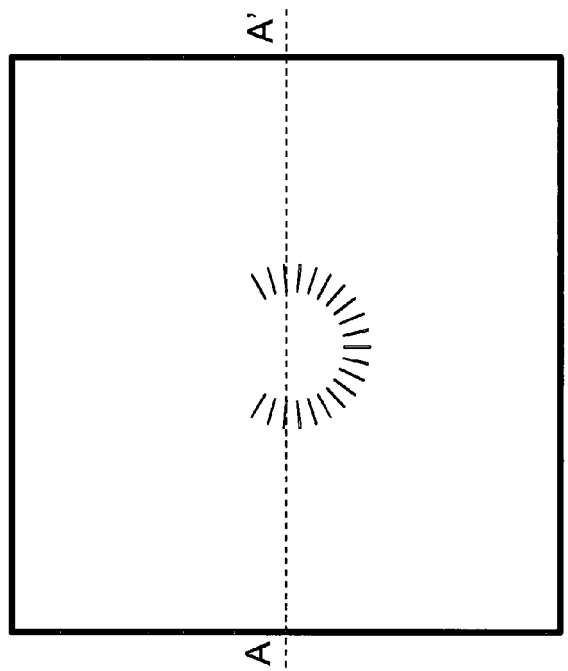
Figure 13D:
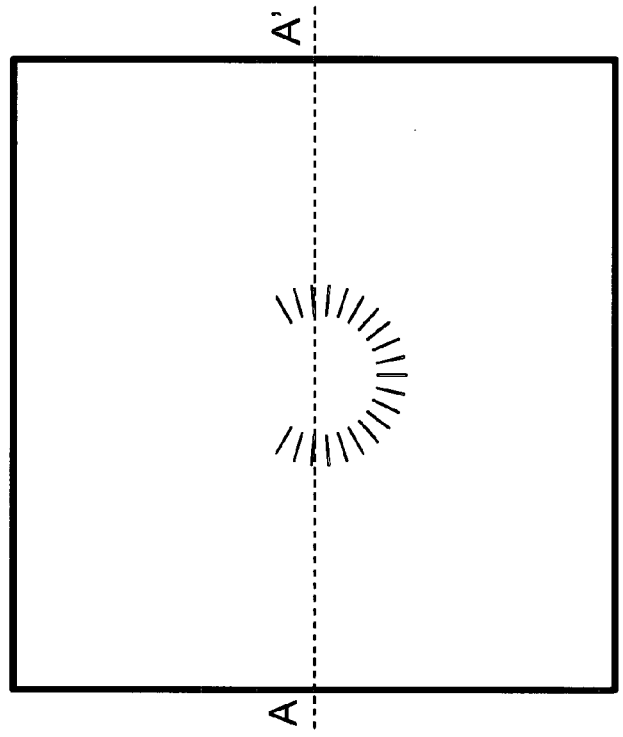
Figure 13E:
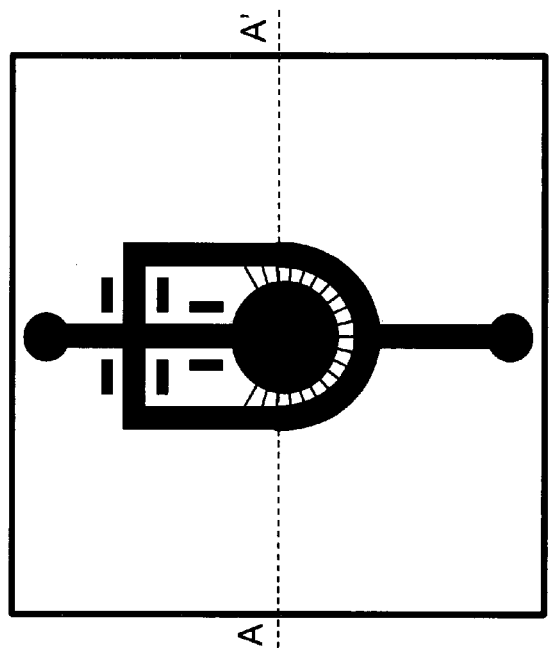
Figure 13G:
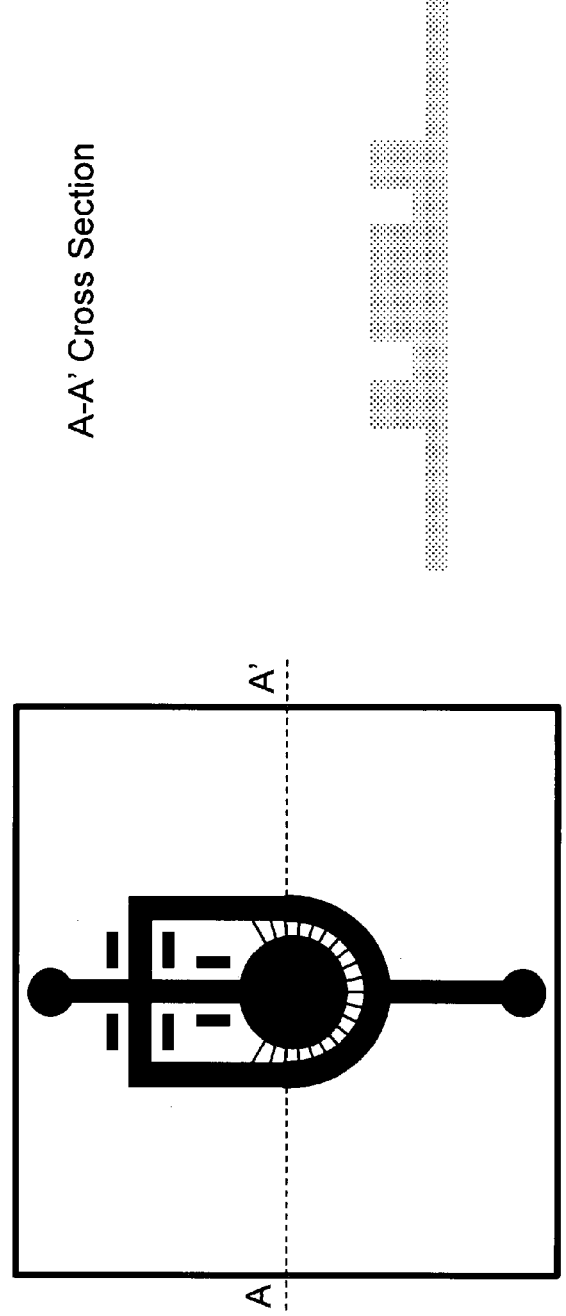
Figure 14C:
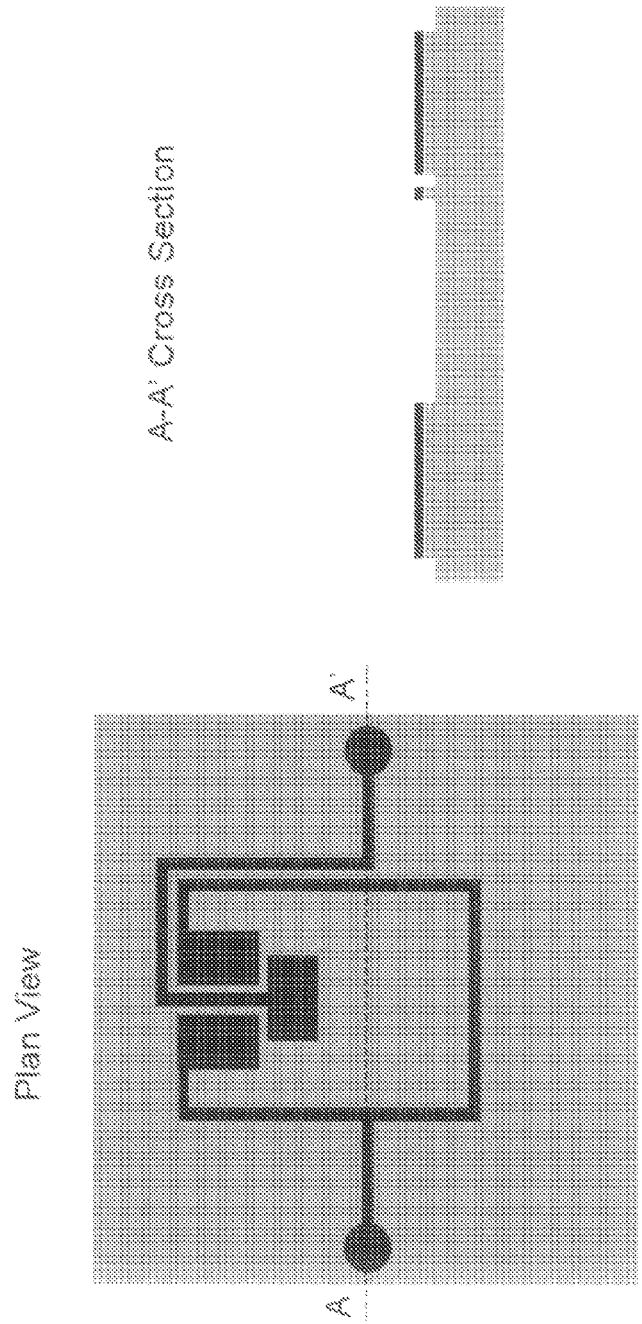
Figure 14E:
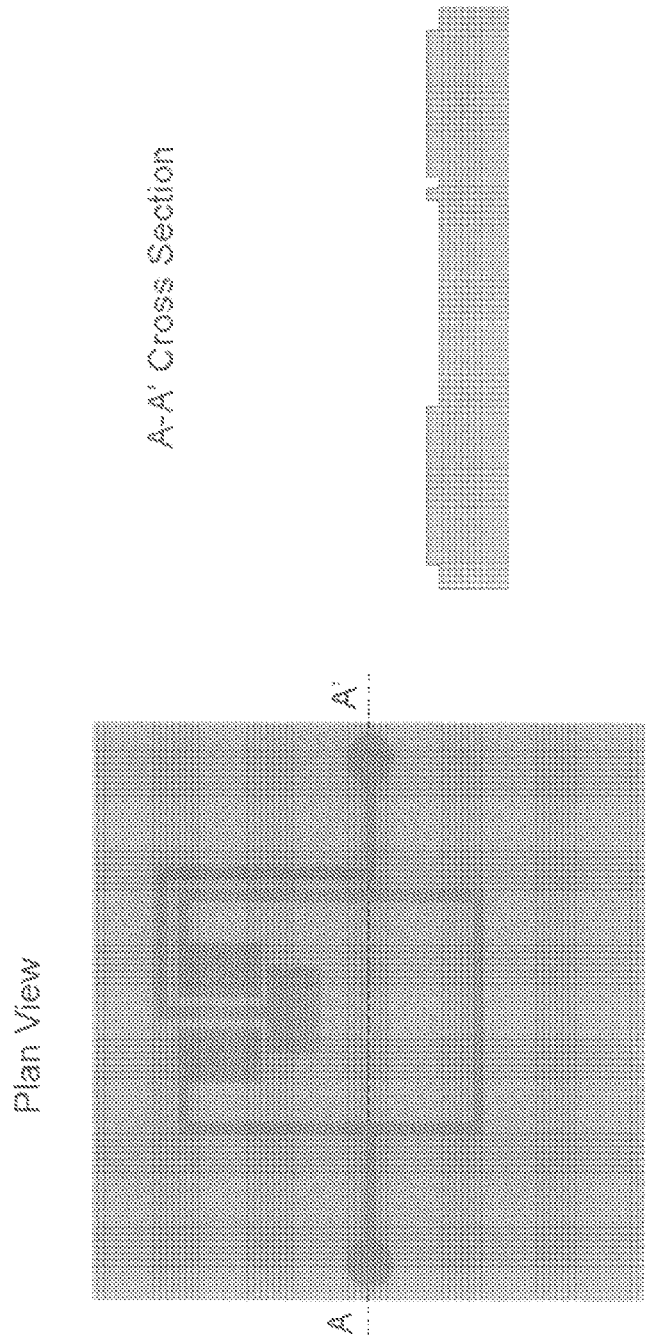
Figure 15:
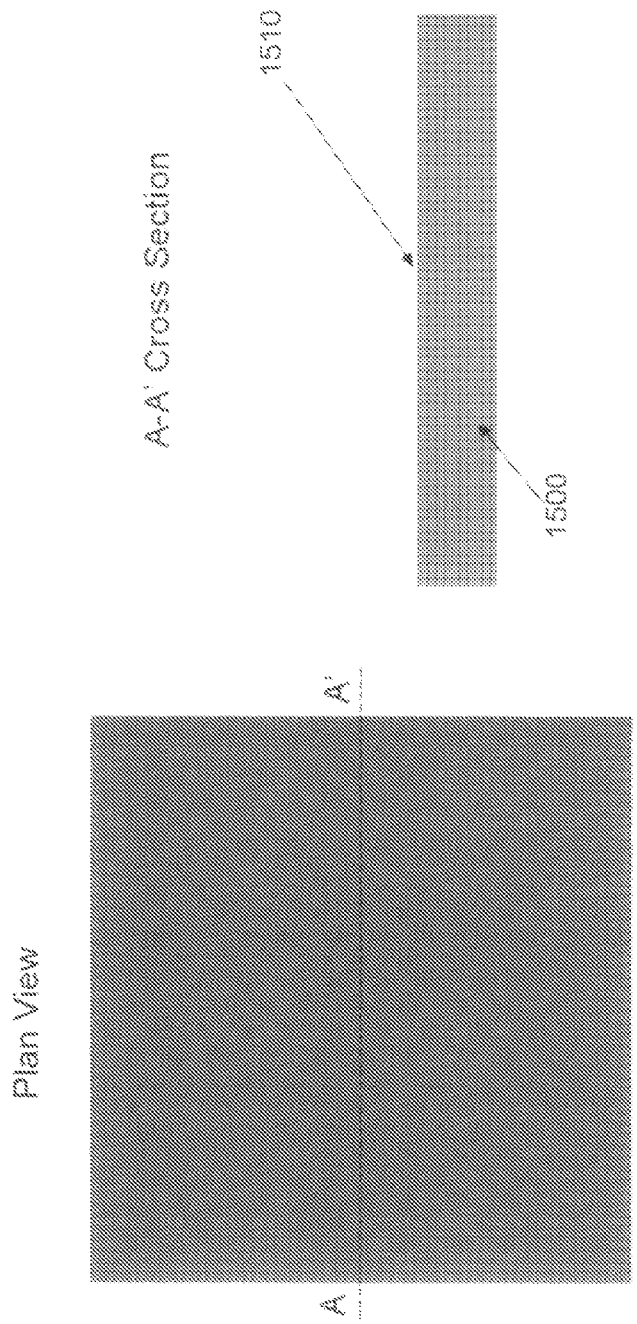
FIG. 15 illustrates an acrylic sheet used in the preparation of the microfluidic device of the invention.

FIGS. 13-17 describe the various steps used to prepare multilayer, integrated devices useful for practicing the subject invention. The microfabrication techniques 25 used to prepare molds for the two elastomer layers are described in FIGS. 13A-H and 14A-E. FIG. 15 describes the semi-rigid plastic substrate used to support the upper layer, FIG. 16 details the molding process and the elastomer monolith assembly. FIGS. 17A-D illustrates the holder, and the final assemble of the device. The particular methods described here are illustrative, and should not be viewed as limiting the scope of the device or the process for fabricating such a device. Numerous analogous materials, steps, dimensions and methods may be used, as is readily understood to those skilled in the art.

FIGS. 13A-13H illustrate the process for preparing a mold useful for making a microfluidic device layer elastomer part. In FIG. 13A, a wafer, 1300, is used as the base substrate for mold fabrication. A pattern of the microfluidic layer that will be made is shown in the inset, 1310. The layer pattern is repeated across the surface of the wafer as indicated by the repeated square regions on wafer 1300. The wafer used is preferably silicon, and may be of any of the standard sizes used in microfabrication foundries. Note however that wafer-based fabrication is not necessary, but is used for convenience. A 4" wafer size allows a substantial number of patterns to be repeated across the surface, and is a size that is commonly available at commercial facilities. Other wafer materials may be used as desired, with the appropriate methods analogous to those described here employed as necessary. These fabrication steps are well-developed in the art.

In order to more clearly focus on illustrating the fabrication process, the microfluidic pattern 1310 is a simplified pattern, yet one that includes enough features to provide for a valved microfluidic device of the type discussed above. As exemplified in the figure, an inlet area 1312 and an outlet area 1314 are provided for access with the external world. Inlet channel segment 1316 leads from the inlet area 1312 to an intersection with a pair of first arm channels 1320a and 1320b, and second arm channel 1322. The pair of first arm channels 1320a and 1320b later merge downstream and lead into outlet channel segment 1328, which ends at outlet area 1314. Second arm channel 1322 leads into well 1324. The well 1324 communicates with the first arm channels via a series of smaller passageways 1326 connecting the two features.

The pattern in the microfluidic layer also includes the recesses of the valve regions in the first and second channel arms. The recesses 1330a and 1330b are defined on either side of each of the first arm channels 1320a and 1320b, respectively. Likewise the recesses 1332 flank the second channel arm 1322. The recesses are voids into which the side walls of the channels (secondary membranes) may deflect when the pressure is changed at the primary membrane, and thereby operate as part of the valve. The recesses thus serve to define the valve region of the channel, although to be functional the primary membrane needs to also be provided at the same region. Note that the primary membrane is defined through the fabrication of the pneumatic control layer, described in FIG. 14.

First, the microfluidic passageways 1326 that connect the well 1324 with the first arm channels 1320a and 1320b are defined on the substrate using standard photolithography techniques. These passageways, also referred to as perfusion channels, are of a smaller height, and thus are defined first, in a step separate from the other fluidic channels and wells. Photoresist is spun onto the wafer 1300, softbaked, and the wafer is irradiated through a reticle defined with the pattern as shown in the plan view of FIG. 13B. Typically a negative photoresist is used, such that the portion defining the channels is irradiated and the rest of the wafer is not: The photoresist is next developed to remove the non-irradiated portion of the resist. The remaining resist may be hard-baked. The resulting wafer and defined resist are depicted in the cross-sectional view of FIG. 13B. As mentioned above, standard photolithographic techniques are employed, and suitable process details, wellknown to those skilled in the art, are readily adapted from, for example, S. O. Kasap, Principles of Electronic Materials and Devices, 2d Ed., McGraw-Hill (2001). Note also that 'maskless' lithography may be used instead. The particular means of arriving at the fabricated structure is not critical.

Next, the wafer surface is etched away using a dry etching process to leave raised portions that define the perfusion channels 1326. Approximately 1 µm of the surface is etched away using a $SF_6$ plasma. For example, using a PlasmaTherm PK-12 RIE, at an RF power of 100 W and a chamber pressure of 60 mTorr, the etch is performed for two minutes. The resulting wafer is illustrated in the cross-sectional view of FIG. 13C. Thereafter the photoresist atop the raised silicon is removed by an oxygen plasma etch, as shown in FIG. 13D. Using the same model plasma etcher, an oxygen plasma is generated at an RF power of 150 W, and a chamber pressure of 100 mTorr, and the wafer is exposed for five minutes to remove the photoresist.

FIG. 13E shows the results of a second photolithography step. As before, a photoresist is spread across the wafer surface. Here, it is preferable to form the resist with a height greater than that of the raised silicon defining the passageways 1326. For example, if the passageways have a height of 1 µm, then the photoresist should be spun on to give a height of at least 1 µm. The photoresist is irradiated, typically through a reticle, and developed to define the pattern of microfluidic channels, wells and recesses described above. The contours of the features are shown in the plan view of FIG. 13E as the dark portion. The cross-sectional profile of FIG. 13E reveals the relative height of the resist and the previously defined passageways 1326.

With the photoresist in place, the remainder of the wafer surface is etched away (FIG. 13F). In this step of the process, a deeper etch is performed in order to create a mold having a deeper channel and chamber. For example, a deep reactive ion etch of 50 µm is made in the wafer using Surface Technology Systems' Advanced Silicon Etching (ASE) System, alternating etching at an RF power of 12 W, $SF_6$ at 130 sccm and passivating at an RF power of 0 W and $C_4F_8$ at 85 sccm, for 20 minutes, according to the manufacturer's protocol. Again, the remaining photoresist is removed using an oxygen plasma treatment, using the same process as described for FIG. 13D. The resulting profile is revealed in the cross-sectional view of FIG. 13G. The two different heights in the wafer surface correspond to the channel and well depth, and the perfusion channel depth.

Finally, the microfluidic layer mold is completed by coating the processed wafer with a fluorocarbon layer, as shown in FIG. 13H. The wafer is, for example, exposed to a $C_4F_8$ plasma in the ASE System at 85 sccm for ten minutes. The resulting fluorocarbon coating is approximately 10 nm thick. The coating serves to prolong the life of the mold by protecting the silicon features and also to improve liftoff of the molded elastomer from the mold due to it being a lower stiction surface. The coating and improved liftoff is particularly useful for the successful molding of elastomer parts that are thin, e.g. less than 100 thick, or even about 70 thick. Note that where the channel depth has been lithographically defined to be about 50 molding a 70 thick part means there is only a 20 portion adjacent to the channel or well.

FIGS. 14A-14E illustrate the process for preparing a mold useful for making a device control layer elastomer part. In FIG. 14A, a wafer, 1400, is used as the base substrate for mold fabrication. A pattern of the microfluidic layer that will be made is shown in the inset, 1410. The layer pattern is repeated across the surface of the wafer as indicated by the repeated square regions on wafer 1400. For convenience the same microfabrication methods and materials used for the first layer are also used here. The pattern is conveniently prepared at the same size as that in the first microfluidic device layer in this exemplification. Note that the first and second layers are to be aligned and bonded together in the final device. The channels and chambers designed in this second layer form the features that will operate with the recesses and secondary membranes defined in the first layer to act as a pneumatically controlled valve. It is also contemplated that a pneumatic-activated device control layer might only be needed to cover a fraction of the microfluidic device layer, depending on the size, complexity and layout of the device channels. Accordingly, the wafer size and/or the pattern size may differ between the two layers.

As exemplified in FIG. 14A, the pattern 1410 contains three microvalves, with two being simultaneously active on one line. There is a first inlet area 1412, leading to paired first control channels 1414a and 1414b, and a second inlet area 1422 leading to a second control channel 1424. The inlet areas function to provide access with the external world, as will be described later. The control channels 1414a and 1414b lead to pneumatic chambers 1416a and 1416b, respectively. Likewise second control channel 1424 leads to pneumatic chamber 1426. The chambers are defined to occupy a space directly above the valve region defined by the recesses in the fluidic layer mold. The channel and chamber systems in this layer do not have an "exit", but are closed end networks that will be pressurized as needed to actuate the valve. Because the chamber 1416a and 1416b are on the same line they will operate in concert, with both being either open or closed.

The fabrication process follows that already described in conjunction with FIG. 13, except that there is only photolithography step for the control layer mold. The photoresist is spin-coated, irradiated, typically through a reticle, and developed to define the pattern of the channels and chambers described above. The contours of the features are shown in the plan view of FIG. 14B as the dark portion. The cross-sectional profile of FIG. 14B reveals the distribution of the photoresist.

The exposed wafer surface is etched away using a dry etching process to leave raised portions that define the control channels (1414a, 1414b, 1424) and chambers (1416a, 1416b, 1426). Approximately 5 μm of the surface is dry etched away using a SF$_6$ plasma, using the PlasmaTherm PK-12 RIE, at an RF power of 100 W and a chamber pressure of 60 mTorr, for ten minutes. The resulting wafer is illustrated in the cross-sectional view of FIG. 14C. Thereafter the photoresist atop the raised silicon is removed by an oxygen plasma etch, as shown in FIG. 14D. Using the same process and equipment as described for FIGS. 13D and 13G, an oxygen plasma is generated at an RF power of 150 W, and a chamber pressure of 100 mTorr, and the wafer is exposed for five minutes to remove the photoresist. The resulting profile is revealed in the cross-sectional view of FIG. 14D.

Finally, the control layer mold is completed by coating the processed wafer with a fluorocarbon layer, as shown in FIG. 14E, using the same C$_4$F$_8$ plasma etch described above, with the same resulting advantages.

FIG. 15 illustrates a semi-rigid sheet 1500 also used in the fabrication of a fluidic device. The sheet is, for example, an acrylic polymer, but also may be chosen from any of polymethyl methacrylate (PMMA), polycarbonate, polystyrene, polynorbornene, polyethylene terephthalate, polyethylene, polypropylene and poly(4-methyl-1-pentene), or other like thermoplastic material, so long as there is an adhesion promoter by which the material can be bonded to the elastomer part. The sheet is to be provided at the same size as the control layer part.

Preferably sheet 1500 is approximately 1.5 mm thick, such that it maintains a two-dimension rigidity. The sheet is to perform (1) as a backing for the elastomer parts to (a) make handling easier and (b) prevent tearing, and (2) as a surface for bonding the elastomer device to a holder. Note that a thinner sheet may be used, but if the sheet no longer maintains a two-dimensional rigidity the above purposes will not be met. The sheet may be thicker, e.g. several mm's in thickness, or more, though at greater thicknesses the extra material becomes superfluous although not detrimental.

One surface of sheet 1500 is to be coated with an adhesion promoter 1510. The promoter is to aid in the bonding of the sheet 1500 to the molded elastomer part, and is needed because of the dissimilarity of the materials of the two parts. An exemplary adhesion promoter is the 1200 Primer (Dow Corning, Midland, Mich.), which is typically used to promote the adhesion of silicone materials to a variety of materials. This promoter is an appropriate choice given that the preferred elastomer is a silicone derivative, polydimethylsiloxane. Other promoters may be selected as appropriate for a given choice of materials for the sheet and the elastomer part, as are known to those skilled in the art of adhesives and bonding of plastics and elastomers.

The adhesion promoter is to be applied to the surface of the sheet just prior to use. Manufacturer's recommendations should be followed as to the timing of application prior to the bonding step for any promoter that is selected.

FIGS. 16A-16K illustrate the molding process for the two layers, the bonding process putting the layers together, creation of the access holes, and the bonding of the assembly to a bottom substrate.

First, as shown in FIG. 16A, the device layer elastomer part is prepared using the mold 1600, as prepared by the steps of FIG. 13. The elastomer precursor is spread over the mold using, for example, a spin-coating technique. Other techniques for distributing the liquid over the mold such a dip coating, dispensing or roll coating may be used without limitation. The elastomer precursor may be selected from the group of materials such as precursors for polyisoprene, polybutadiene, polyisobutylene, polyurethane, silicone, and polysiloxane. The precursors may be liquid formulation of either monomers, oligomers or short polymers that are capable of polymerization, further polymerization or crosslinking and the like such that an elastomer monolith results. One preferable elastomer is a polydimethylsiloxane (generally referred to as PDMS). Numerous formulations for PDMS elastomers are commercially available, such as Sylgard 184 (Dow Corning, Midland, Mich.).

To prepare the device layer elastomer, for example, Sylgard 184 is dispensed over the wafer with mold, 1600, and by spin-coating, a layer of the PDMS precursor 1610 is formed with a height of 70 μm. The height of elastomer ultimately obtained should be considered when determining the height of the precursor to be spread over the mold. For example, any shrinkage or contraction that might occur when the precursor is cured should be accounted for.

The height of the elastomer in relation to the height of the mold features determines the thickness of the membrane between the channel feature and the next layer of elastomer, the control layer, in the final assembly. In locations where the channel portion is to be the valve region, the membrane will be the primary membrane of the valve, and its performance and activation parameters will be determined by the thickness established in this step. A thickness of about 20 μm is preferable, though the thickness may reasonably vary. As one skilled in the art would know, a thinner membrane may not be as durable, but the valve would be capable of activation at lower pressure. Conversely, a thicker membrane would be more robust and durable, but would require greater operating pressures to be activated. Membranes thicker than about 100 μm generally require activation pressures that are high enough to damage the material. Furthermore the thickness makes it difficult to activate the valve into a fully closed position and thus is not preferred where complete closure of the valve is necessary.

Figure 16B:
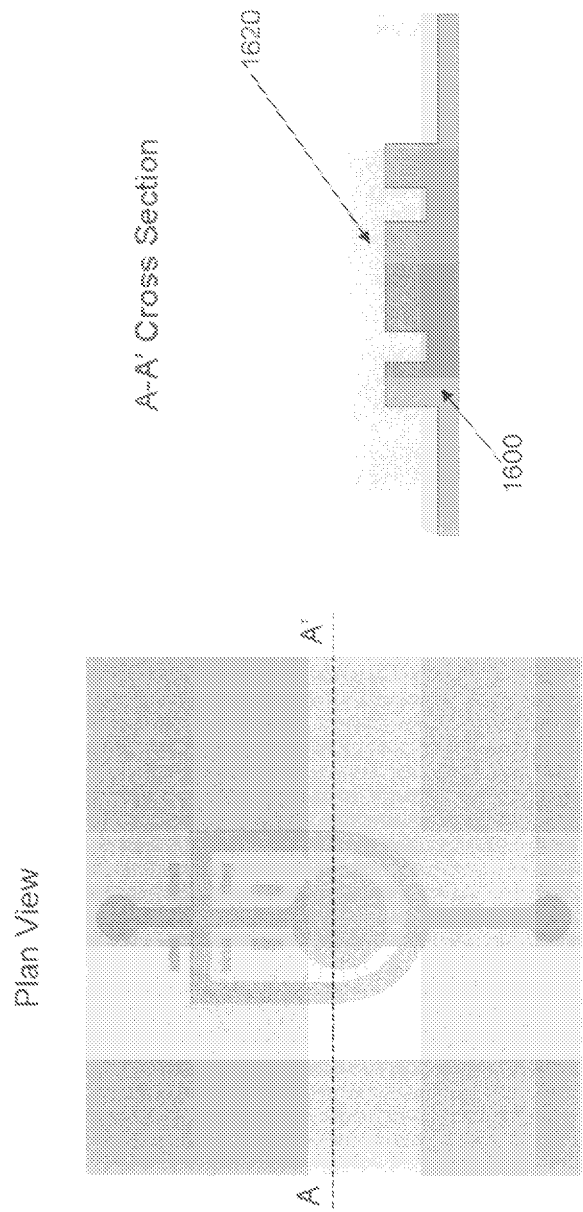

After spin-coating the PDMS precursor, the material is partially cured by treatment in a 60° C. convective oven for one hour. FIG. 16B shows the mold 1600 with the partially cured elastomer part 1620 in place on the mold.

In parallel, the control layer elastomer part is prepared with a similar material. FIG. 16C illustrates the mold 1630, prepared as described in FIGS. 14A-E, and a fixed volume of the elastomer precursor dispensed over the mold 1640. The volume is determined by a calculation of the volume of the part, given the mold topography and the desired thickness of the part.

Figure 16D:
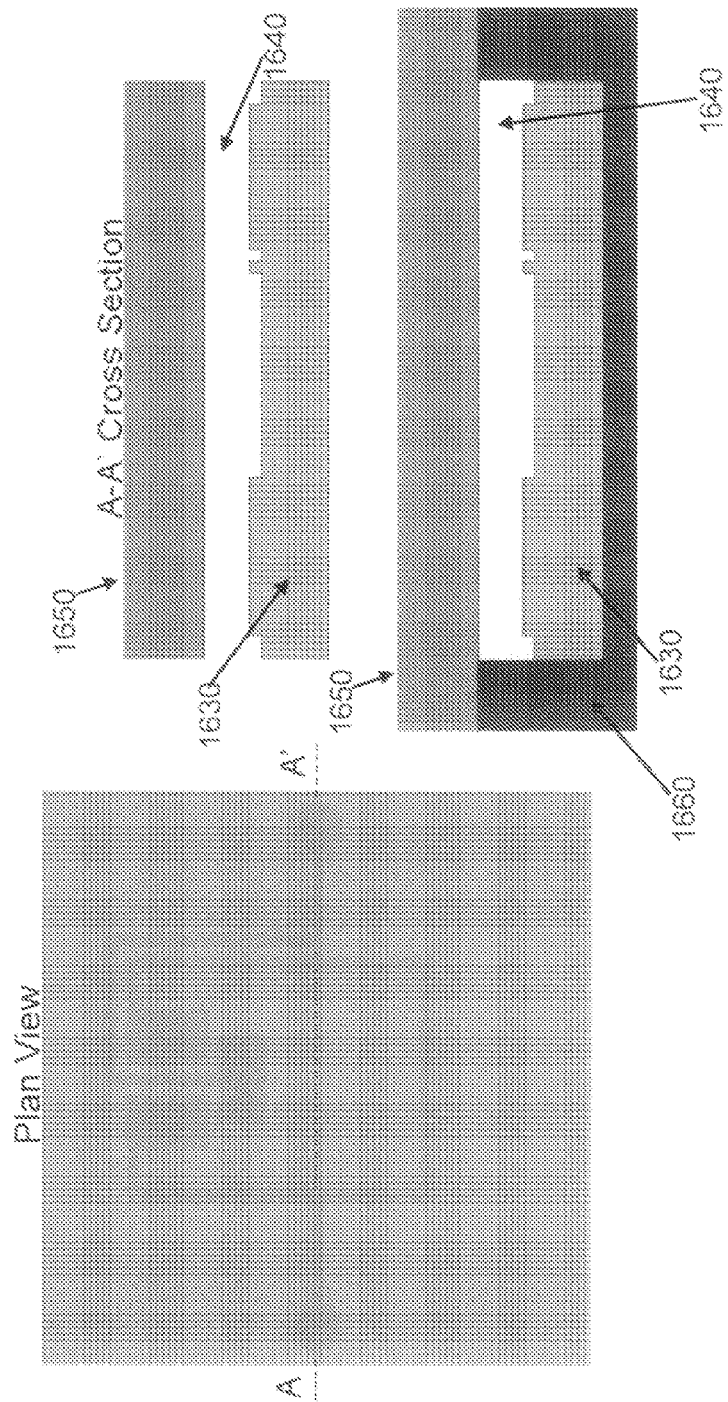

The semi-rigid sheet described in FIG. 15 is then placed over the top of the dispensed elastomer precursor with the side bearing the adhesion promoter contacting the elastomer. For example, two methods for performing this are illustrated in FIG. 16D. The sheet 1650 may be simply laid on top of the elastomer, whereby gravity and surface tension work to bring the sheet flat against the entire surface of elastomer 1640. In another embodiment, the mold 1630 and elastomer 1640 may be placed within a fixed height spacer fixture 1660, with the sheet 1650 positioned over the edges of the spacer to ensure that the sheet lies parallel to the molded surface, and a molded part with a uniform, fixed height consistent from part to part is obtained. For example, the mold 1630 is placed within the fixed height spacer 1660. A fixed volume sufficient to form a 200 thick layer of Sylgard 184 is dispensed onto the mold. Thereafter, a 1.5 mm thick acrylic sheet 1650, with an adhesion promoter coated on one side, is placed on top of the spacer fixture 1660 such that the promoter coating contacts and spreads the Sylgard 184 out over the entire mold surface.

Figure 16E:
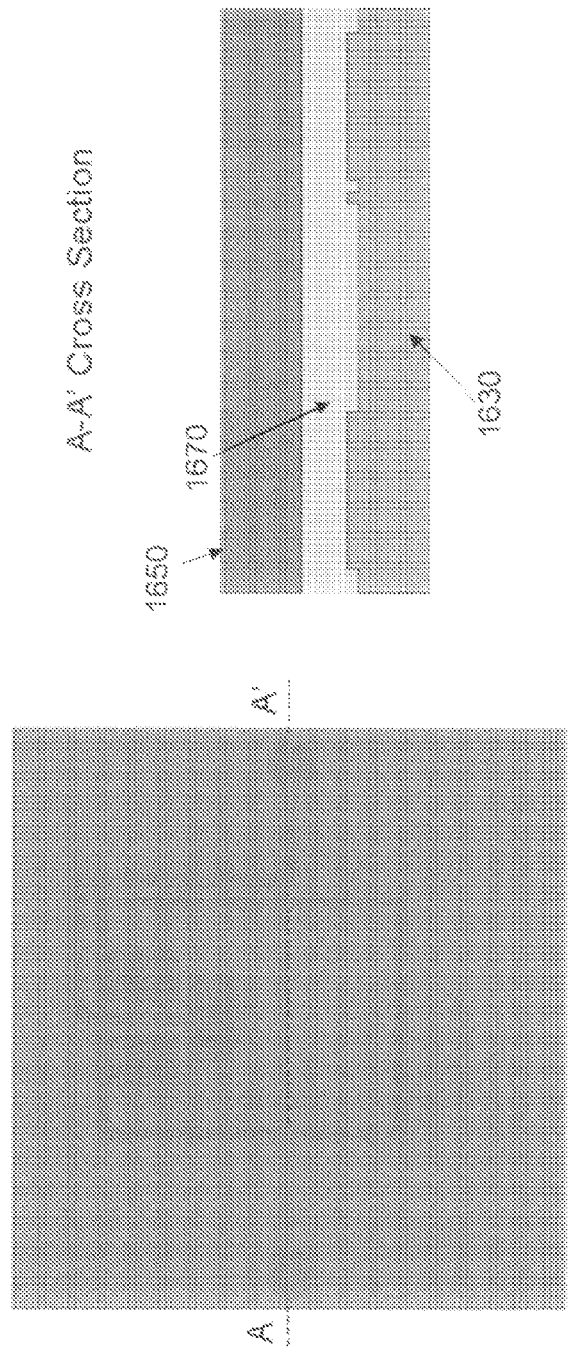
Figure 16G:
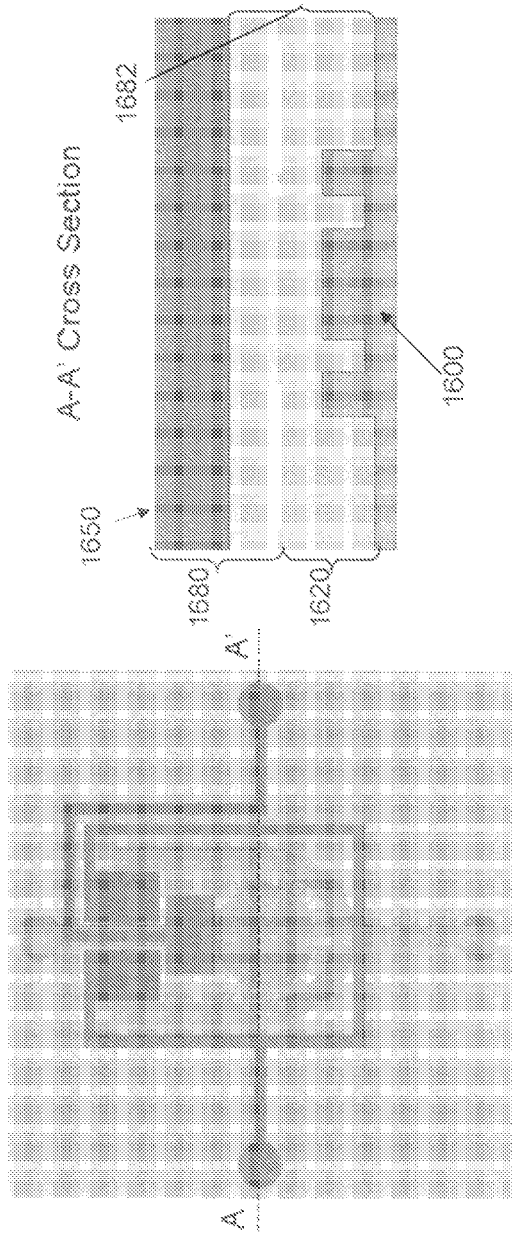
Figure 16H:
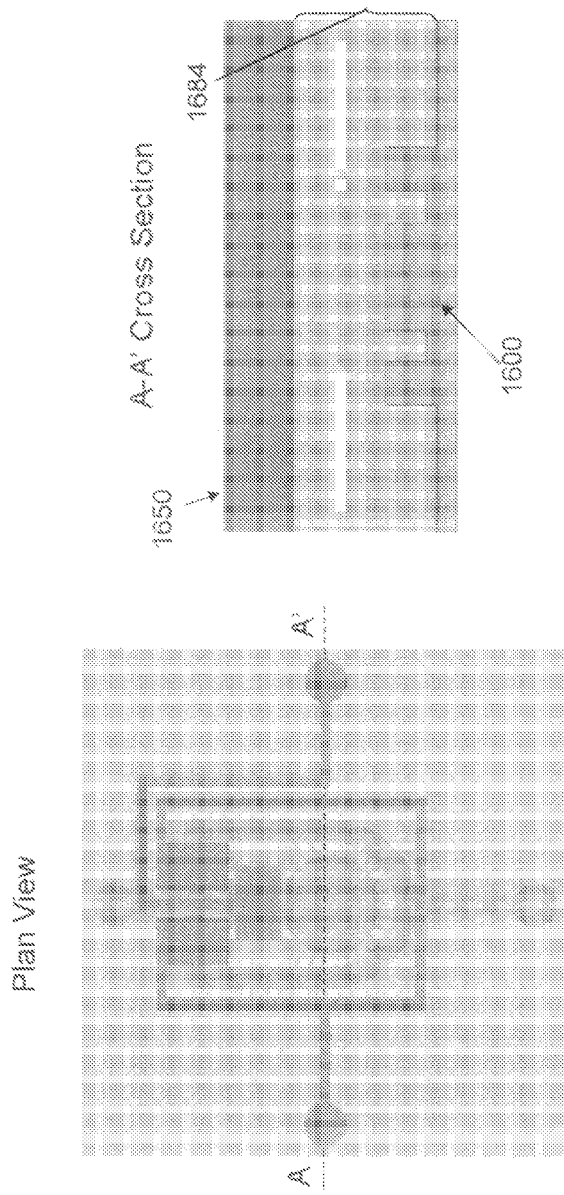

After preparing the assembly, the elastomer material is partially cured, again by treatment in a 60° C. convective oven for one hour. FIG. 16E shows the mold 1630 with the partially cured elastomer part 1670 in place on the mold, and the semi-rigid sheet 1650 affixed to the top of the elastomer part. When the assembly has cooled to room temperature, the now joined sheet and elastomer 1680 is peeled off of the mold, as shown in FIG. 16F. The flexible yet semi-rigid backing sheet permits the elastomer part to be readily peeled off the mold surface in an easy motion with little risk of tearing the control device layer elastomer part.

The upper layer, the control device layer with the backing sheet 1650 is aligned over the device layer mold 1600 and molded part 1620 such that the operational features of the valves are properly positioned, and then contacted together for bonding. This process may be performed with the aid of a standard mask aligner, such as a Quintel Q-4000 Series mask aligner. The assembly now comprises the lower mold 1600, the device layer molded part, the control layer molded part, and the semi-rigid sheet, as shown by the cross-sectional view of FIG. 16G. The elastomer parts 1682 of the assembly are then treated in a 60° C. convective oven for one hour to yield a cured and bonded part 1684, shown in FIG. 16H

Figure 16I:
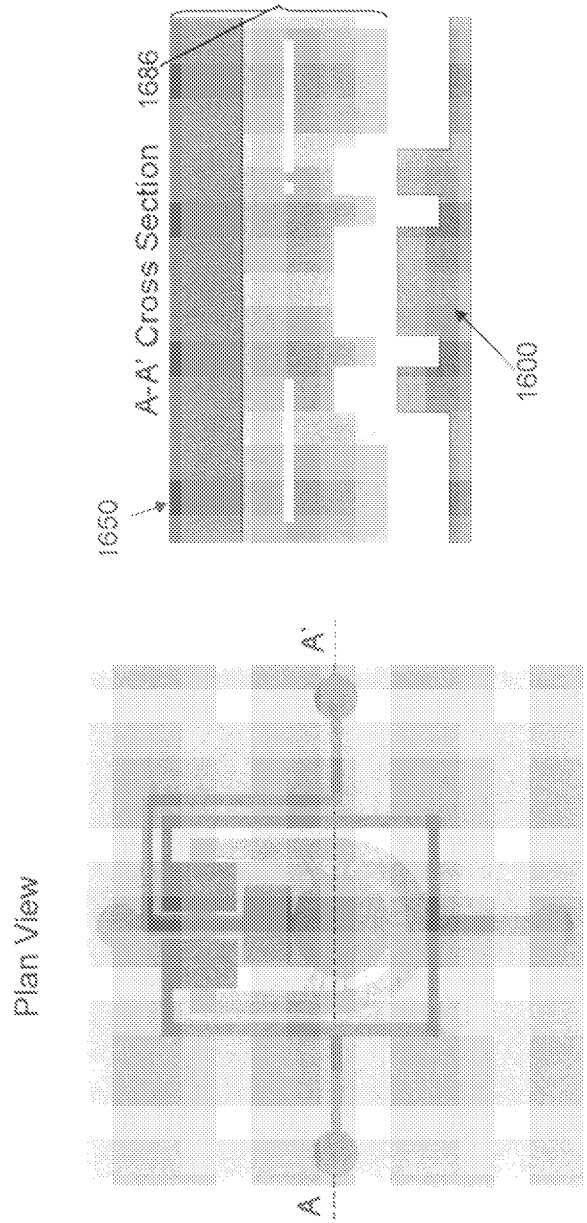

When the assembly has cooled to room temperature, the now joined sheet and bonded, cured elastomer 1684 is peeled off of the mold, as shown in FIG. 16I. Again, the flexible yet semi-rigid backing sheet permits the elastomer part to be readily peeled off the mold surface in an easy motion with little risk of tearing the bonded elastomer parts. The mold 1600 may be reused again, and the device assembly 1686 is taken for further processing.

Next, access holes are formed in the device 1686 by piercing, drilling, ablating, or laser cutting. The access holes are bored through the entire height of device 1686. The location of the access holes correspond to the areas designated as the inlet areas or outlet areas of each of the two layers. Referring to the plan view drawing of FIG. 16J, there are four access holes formed in the device 1686, two that address the fluidic device layer (inlet, 1690; outlet 1692) and two that address the control layer inlets (1694 and 1696). The two access holes that address the control layer also appear in the cross-sectional view of FIG. 16J.

The holes are preferably formed by laser cutting techniques. The laser may be either a continuous wave (CW) mode or pulsed mode type. Although greater care must be used when cutting with a CW laser because of the possibility of overheating or charring the material, operation with CW lasers is possible so long as the device is no thicker than several millimeters. For example, a VersaLaser, from Universal Laser Systems (Scottsdale, Ariz.), operated at 25 W and controlled to move at 40% arm speed over steps of 1000 points per inch to cut the access holes successfully bores holes through devices comprising a 1.5 mm sheet and a ~300 elastomer monolith. The holes are cut by controlling the laser to follow a circular pattern around the center point of the hole location via the software controls provided with the instrument. If a thicker device undergoes charring during laser cutting with a CW laser then operation with a pulsed mode laser is preferred.

The bottom surface of device 1686, bearing the molded imprint of the fluidic device layer, is next bonded to a rigid substrate to enclose the channels and chambers of the fluidic layer, as well as to seal off the bottom of the access holes. The substrate preferably contains surface hydroxyl groups to make the surface amenable to bonding with the elastomer material. For Example, substrates such as glass, metal oxides, silicon with an oxide surface are suitable, providing both rigidity and the necessary affinity for bonding to the elastomer. FIG. 16K shows a glass substrate 1696 bonded to the device 1686 to form the functional device 1698. The glass substrate 1696 is precut to the size of the device. Then, both the glass surface and the PDMS surface of device 1686 are each treated with an oxygen plasma using the PlasmaTherm PK-12 RIE, at an RF power of 40 W and a chamber pressure of 2 Torr for 40 seconds. After oxygen plasma treatment the two pieces are aligned and contacted. As a result of the treatment the two surfaces will bond together to make a leak-proof seal.

The device assembly 1698 is fully capable of use as a microfluidic device with functioning pneumatically controllable valves. For greater ease of use and to enable interfacing the device with automated robotic systems, the device 1698 may be integrated with a housing or a holder that facilitates putting reservoirs of fluids in communication with the device, and connecting fluid lines and pneumatic controls to the device. When low pneumatic pressure is required, gravity-driven flow can be used by tilting the device 1698.

Figure 17A:
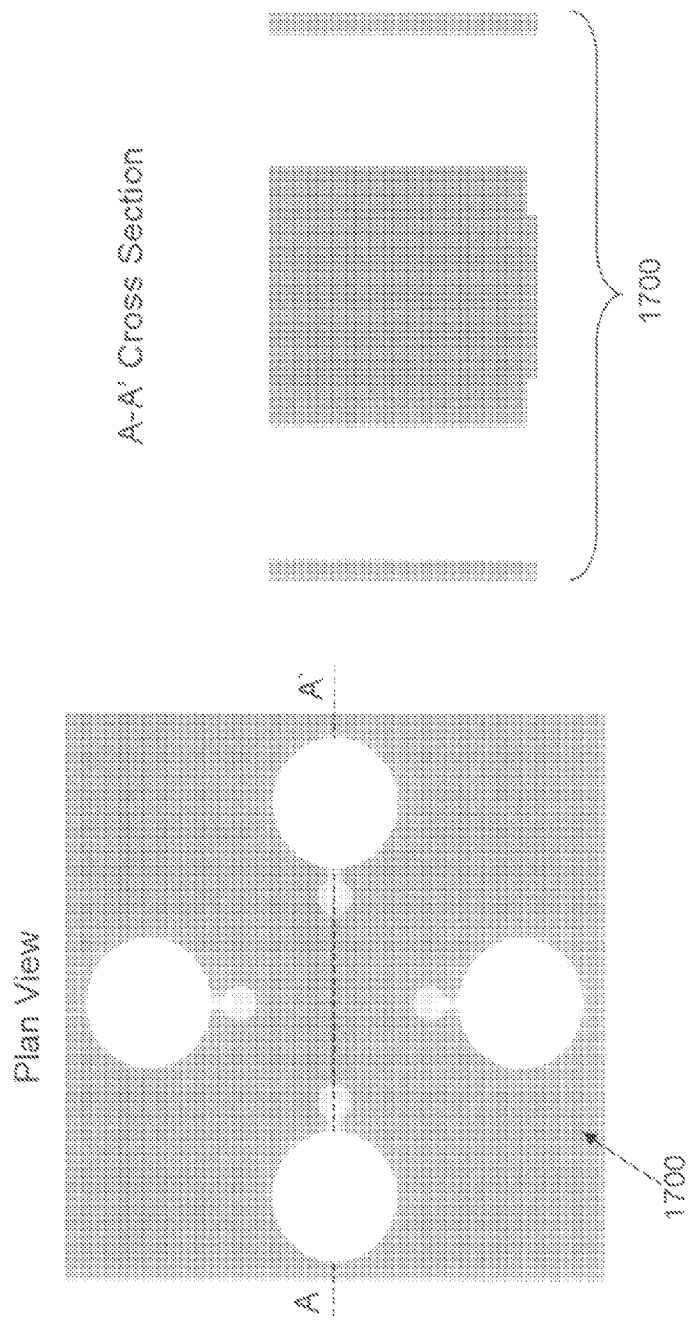

FIGS. 17A-17D illustrates the design and fabrication of a holder that integrates with the microfluidic device and serves to facilitate access from the external world to the fluidic and control layers inside the device. The holder is assembled from two separate parts. The upper part 1700 is illustrated in FIG. 17A. This upper part comprises a body with a plurality of holes opened through from the top surface to the bottom surface. The side wall of each hole will form the side of a reservoir or connector port in the completed holder. The part also comprises a plurality of shallow cavities at the bottom surface of the part. The cavity openings may be circular or rectilinear or a combination thereof with respect to the bottom surface. Generally, the depth of these cavities is uniform, though uniformity is not required. One cavity is provided adjacent to each hole, positioned to intersect with a side wall of the adjacent hole. Thus, the top surface has a roughly circular opening, and the bottom surface has an eccentric opening, defined by the combined area of the hole and the cavity.

The holes may be shaped for a variety of special purposes. For example, where the hole is to be used as a liquid reservoir, the hole may be dimensioned to be that of a standard microwell plate, e.g. a 96-well plate or a 384-well plate or other sizes. The standard sizes are set forth in the SBS standards and can be found on www(.)sbsonline(.)org/msdc/pdf/text1999-04.pdf. Also, the holes themselves may be positioned relative to one another at standard distances that conform to SBS standards. The purpose of using standardized well shapes and distances is to facilitate interfacing the part with automated dispensing and handling systems. The hole may also function as a connection port, e.g. for receiving the tips, couplers or connectors of fluid (liquid or gas) lines. There are numerous standard interfaces for such connections, and any of these may be employed in the design of the part. One common example of a connection is a Luer connector, though many others are possible. The hole, shaped as a Luer receiver, would permit the rapid insertion of a Luer-tipped syringe body. Note also that the various holes may be prepared with differently shaped or sized holes, depending on the purpose of the hole and the underlying access hole in the fluidic device with which it communicates.

The part itself may be made of any suitable durable material, with metal or plastic being preferred. The part may be machined, cast or molded, according the material type chosen. Molded plastic parts are preferred for their low cost.

Standard injection molded methods are suitable for making the part, being able to provide the necessary precision and detail of shape desired.

FIG. 17B shows the lower part 1710 of the holder body. As is apparent in the plan view, the upper surface comprises a plurality of holes. These holes are positioned to align with the cavities formed in the lower surface of upper part 1700, with little or no overlap with the opening of the holes in the upper part. The lower surface has a cavity sized in all dimensions to house the microfluidic device 1698. The holes in the upper surface lead into the cavity opened in the lower surface, as illustrated in the cross-sectional view of FIG. 17B. Also, the upper surface of the lower part largely covers the hole opening in the bottom of the upper part, thus forming in the completed part the bottom of a reservoir defined by the hole in the upper part.

Figure 17C:
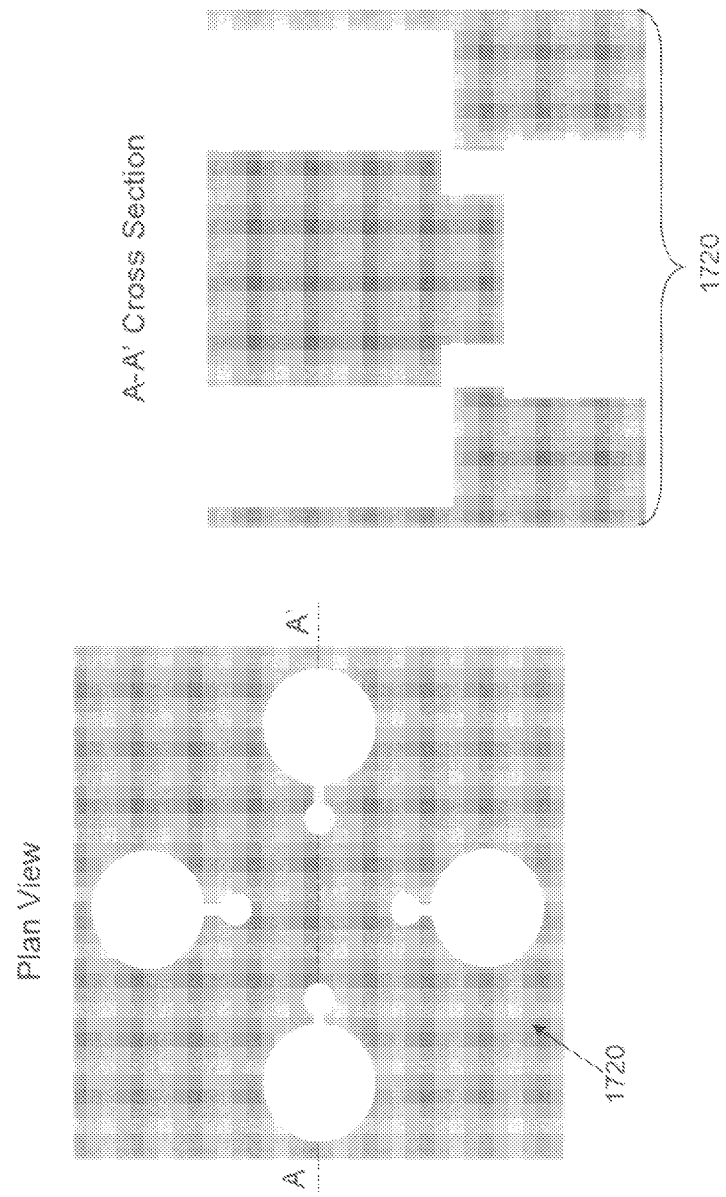

As shown in FIG. 17C, the two parts are mated, with the upper part's cavities and the lower parts' holes aligned, and joined by, for example, thermal diffusion bonding, adhesive bonding using a pressure sensitive adhesive, solvent welding, or other technique for joining two plastics as is known in the art, to give the completed holder 1720. Thus, upper part 1700 and lower part 1710 were formed of acrylic by injection molding. The parts were then aligned and bonded using a Carver Lab Press to apply 0.5 tons of force, while heating the surface to 106° C. and holding for 10 minutes.

Note that the number of holes in the upper part generally correspond to the number of access ports formed in the fluidic device (e.g. 1698). The holes in the upper part 1700 communicate with the access holes, but are generally not positioned directly vertically above the access holes, although if the space permits they may be so positioned. Often, due to the density of access holes in the design, the larger holes used in the holder 1730 need to be offset from a position vertically above the access holes. The two-part holder design shown in FIG. 17 is illustrative of one means to achieving such a design for larger external ports, reservoirs and connectors to communicate with the smaller access ports to the internal network of channels and chambers in the fluidic device.

The last step in assembling the integrated microfluidic device is shown in FIG. 17D. The microfluidic device 1698, is positioned within the cavity of the lower part of holder 1720, with the semi-rigid sheet 1650 contacting the holder. An adhesive is conveniently applied to join the two parts. For example, where the holder and the sheet are both acrylic, an acrylic cement, IPS-3, from TAP Plastics (Stockton, Calif.), is used to join the parts to give integrated device 1730.

The design of the microfluidic device used to illustrate the fabrication process was simplified for the ease of presentation and explanation. The steps used in the process are generally applicable to a wide variety of device configurations, including devices of much greater size, complexity and density, as would be appreciated by those skilled in the art of fluidic device design and fabrication. For example, the devices described throughout this disclosure are all capable of fabrication by these methods.

What is claimed:

1. A microarray culture system, comprising
(a) a substrate,
(b) formed in said substrate, a plurality of microfluidics passageways, each having (i) a well for receiving particles therein, (ii) an inlet channel segment, (iii) an outlet channel segment, (iv) a channel intersection segment having a first channel arm that communicates the inlet and outlet channel segments, and a second channel arm communicating the inlet channel segment with the interior of said well, where the first channel arm flows around a portion of the well, and (v) a porous barrier through which fluid, but not cells, in said well can perfuse from the well into said first arm,
(c) associated with each passageway, a first valve disposed in said first channel arm for controlling the flow of fluid from the inlet channel segment into the first channel arm, and a second valve disposed in said second channel arm for controlling the flow of fluid from the inlet channel segment into the passageway well,
(d) a microchannel well-distribution network adapted for supplying input fluid to each of a selected one or more of wells in the passageways, under the control of a plurality of valves associated with the network,
(e) first and second microchannel valve-supply networks for supplying fluid pressure to first and second valves in said passageways, respectively,
(f) a plurality of reservoirs, each in fluid communication with a channel in said well-distribution network or in said valve-supply network, and
(g) a controller for supplying pressurized fluid to selected ones of said reservoirs, thereby to supply fluid to a selected one or more of said microfluidic passageways and to selected ones of said valves.

2. The system of claim 1, which contains N passageways, wherein said microchannel distribution network has X separate valved channels, where $X=2 \log_2 N$.

3. The system of claim 1, wherein said first and second valve-supply networks are operable to supply fluid pressure simultaneously to all of said first and second valves, respectively.

4. The system of claim 1, which further includes a detector by which the presence or absence of cells in a passageway intersection can be determined, and a controller for sequentially activating said second and first valves for capturing a cell in such intersection in the associated well.

5. The system of claim 1, wherein said reservoirs include at least one cell reservoir for holding cells to be introduced into said passageways, and at least one reagent reservoir for holding a solution to be perfused through said passageways, and which further includes a sample-control network for controlling the flow of fluid in said cell and reagent reservoirs to said well-distribution network.

6. The system of claim 5, wherein said controller operates in one mode to (i) control the sample-control network to direct fluid in said cell reservoir into said well-distribution network, (ii) to control the well-distribution network to direct fluid from said cell reservoir to a selected passageway, and (iii) control said first and second valve-supply networks to open the second valve and close the first valve associated with the selected passageway.

7. The system of claim 5, wherein:
said controller operates in one mode to open said first valve, and close the second valve in each passageway, so that a cell-culture medium contained in a reagent reservoir flowing from a device inlet to a device outlet can exchange solute components with cell culture medium in each well across said porous barrier; and
said controller operates in one mode to close said first valve, and open the second valve of said passageways, so that a medium flowing from a device outlet to a device inlet will carry the cells in the device wells out of the device.

8. A microfluidics culture device, comprising
(a) a substrate,
(b) formed in said substrate, a microfluidics passageway having (i) a well for receiving particles therein, (ii) an inlet channel segment, (iii) an outlet channel segment, (iv) a channel intersection segment having a first channel arm that communicates the inlet and outlet channel segments, and a second channel arm communicating the inlet channel segment with the interior of said well, where the first channel arm flows around a portion of the well, and (v) a porous barrier through which fluid, but not cells, in said well can perfuse from the well into said first arm, and (c) a valve disposed in said second channel arm, operable to control the flow of fluid from the inlet channel segment into said well, wherein a cell carried in a fluid moving through said inlet segment can be diverted into said well by opening said valve, and once diverted into said well, can be captured therein, with fluid flowing through said passageway, by closing said valve, and culture medium flowing through said first arm can exchange solute components with culture medium within said well by diffusion of such components across said porous barrier.

9. The device of claim 8, where said valve is a pneumatic valves having two or more flexible membranes forming wall portions in valved regions of said second channel arm.

10. The device of claim 9, wherein said two or more flexible membranes include a primary membrane and one or more secondary membranes that are each joined to said primary membrane at a common edge, and the valve further includes a chamber formed in said substrate, separated from said second channel arm by said primary membrane and adapted to receive a positive or negative fluid pressure, thus to deform said primary membrane, wherein deformation of said primary membrane causes said one or more secondary membranes to deform and the combined deformation of the primary and secondary membranes is effective to switch the condition of the valve between its open and closed states.

11. The device of claim 8, which further includes another valve disposed in said first channel arm, operable to control the flow of fluid from the inlet channel to the outlet channel.

12. The device of claim 11, wherein the first channel arm has a pair of branches that flow around opposite sides of the well, and said another valve includes a pair of valves controlling fluid flow through each branch.

\* \* \* \* \*